(12) United States Patent
Adachi et al.

(10) Patent No.: US 7,922,885 B2
(45) Date of Patent: Apr. 12, 2011

(54) DEVICE FOR TRANSPORTING LIQUID AND SYSTEM FOR ANALYZING

(75) Inventors: Sakuichiro Adachi, Hachioji (JP);
Kunio Harada, Hachioji (JP); Hideo Enoki, Kasumigaura (JP); Isao Yamazaki, Ryugasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1189 days.

(21) Appl. No.: 11/430,857

(22) Filed: May 10, 2006

(65) Prior Publication Data

US 2006/0254933 A1   Nov. 16, 2006

(30) Foreign Application Priority Data

May 13, 2005   (JP) ................... 2005-140581

(51) Int. Cl.
*G01N 27/26* (2006.01)
(52) U.S. Cl. ............ 204/450; 204/600; 422/82; 422/99; 422/100; 436/150; 436/164; 436/180
(58) Field of Classification Search .................. 422/100, 422/99, 82, 82.01, 82.02, 81; 204/450, 600–604, 204/643–645, 672; 436/149–150, 164, 180; 205/775
See application file for complete search history.

(56) References Cited

U.S. PATENT DOCUMENTS

| | | | |
|---|---|---|---|
| 3,479,141 A | 11/1969 | Smythe et al. | |
| 4,259,291 A | 3/1981 | Smythe | |
| 4,357,301 A | 11/1982 | Cassaday et al. | |
| 6,565,727 B1 | 5/2003 | Shenderov | |
| 2002/0039797 A1* | 4/2002 | Bonde et al. ................... 436/518 |
| 2003/0048541 A1* | 3/2003 | Kroupenkine et al. ....... 359/665 |
| 2004/0058450 A1* | 3/2004 | Pamula et al. ................ 436/150 |
| 2004/0208794 A1* | 10/2004 | Karg et al. .................... 422/100 |
| 2004/0211659 A1* | 10/2004 | Velev ............................ 204/164 |

FOREIGN PATENT DOCUMENTS

| | | |
|---|---|---|
| JP | 58-44349 | 3/1983 |
| JP | 03-127623 | 5/1991 |

(Continued)

OTHER PUBLICATIONS

Michael G. Pollack et al., "Electrowetting-Based Actuation of Liquid Droplets for Microfluidic Applications", Applied Physics Letters, vol. 77, No. 11 (Sep. 11, 2000), pp. 1725-1726.

(Continued)

*Primary Examiner* — Alexa D Neckel
*Assistant Examiner* — Jennifer Dieterle
(74) *Attorney, Agent, or Firm* — Stites & Harbison PLLC; Juan Carlos A. Marquez, Esq.

(57) ABSTRACT

In a device for transporting liquid, liquid to be transported is enclosed by an oil droplet, which is fractionated with air, for manipulation. Moreover, as a method for supplying liquids wherein a plurality of liquids are enclosed by an oil droplet sequentially and treated, liquid enclosed by an oil droplet is formed by associating one oil with one liquid in a liquid introducing section. According to the present invention, even in the case where a plurality of liquids are manipulated, it is possible to manipulate stably without affecting other liquids. Moreover, it is possible to treat as a liquid enclosed by an oil droplet successively in the device for transporting liquid, thereby allowing the invention to be applied to a system for analyzing easily.

13 Claims, 26 Drawing Sheets

FOREIGN PATENT DOCUMENTS

| | | |
|---|---|---|
| JP | 10-267801 | 3/1997 |
| JP | 2001-310465 | 11/2001 |
| WO | WO-02/066992 A1 | 8/2002 |
| WO | WO-2004/030820 A2 | 4/2004 |

OTHER PUBLICATIONS

Jesse Fowler et al., "Enhancement of Mixing y Droplet-Based Microfluidics", 2000 IEEE, pp. 97-100.

M. Vallet et al., "Electrowetting of Water and Aqueous Solutions on Poly(ethylene Terephthalate) Insulating Films", Polymer, vol. 37, No. 12 (1996), pp. 2465-2470.

Vijay Srinivasan et al., "Clinical Diagnostics on Human Whole Blood, Plasma, Serum, Urine, Saliva, Sweat, and Tears on a Digital Microfluidic Platform", Micro Total Analysis Systems 2003, 4 pages.

Vijay Srinivasan et al., "Protein Stamping for Maldi Mass Spectrometry Using an Electrowetting-Based Microfluidic Platform", Lab-on-a-Chip: Platforms, Devices, and Applications Conference 5591 (Oct. 25-28, 2004), 7 pages.

Office Action from Chinese Patent Office issued Sep. 17, 2009, in Chinese and English.

Vijay Srinivasan et al., "An Integrated Digital Microfluidic Lab-on-a-Chip for Clinical Diagnostics on Human Physiological Fluids", The Royal Society of Chemistry, (2004), vol. 4, pp. 310-315.

Richard B. Fair et al., "Integrated Chemical/Biochemical Sample Collection, Preconcentration, and Analysis on a Digital Microfluidic Lab-on-a-Chip Platform", Proc. SPIE, vol. 5591 (2004); cover sheet and pp. 113-122.

Office Action from Japanese Patent Office, dated Apr. 13, 2010.

\* cited by examiner

DEVICE FOR TRANSPORTING LIQUID AND SYSTEM FOR ANALYZING

INCORPORATION BY REFERENCE

The present application claims priority from Japanese application JP2005-140581 filed on May 13, 2005, the content of which is hereby incorporated by reference into this application.

BACKGROUND OF THE INVENTION

The present invention relates to systems for manipulating liquid on a substrate, and especially to systems for analysis or reaction wherein multiple liquids are transported.

As an analyzer for detecting the amount of ingredient contained in a sample, a spectral analyzer is widely used, wherein a white light from a halogen lamp or the like is irradiated at a reaction liquid, which is a mixed solution of a sample and a reagent, and then a light having transmitted through the reaction liquid is dispersed by means of a diffraction grating to extract a necessary wavelength component and determine its absorbancy, thereby measuring the amount of a desired ingredient. Alternatively, a white light may be irradiated at a reaction liquid after been dispersed with a diffraction grating. In these analyzers, conventionally, a sample and a reagent are dispensed into a reaction container made of plastic or glass, and are mixed to provide for a reaction liquid, at which light is irradiated to measure the amount of ingredient.

However, recently, for the purpose of reduction in the reagent cost and in the environmental load, there is a need for minimalizing the amount of reaction liquids used for analysis, and with the conventional scheme for minimalizing the amount of reaction liquids, the handling of liquid becomes difficult, and the scheme also has a problem that accurate measurements can not be made due to air bubbles generated during the dispensing and mixing. For this reason, there is a need for techniques to manipulate a minimal amount of liquid accurately.

As one method for manipulating a minimal amount of liquid, there is a method for transporting liquid on electrodes formed in a flat substrate, under an electrical control. In this one typical method, a liquid to be transported is converted into granular liquids, which are then sandwiched in between two opposing substrates, in which a plurality of electrodes are formed, and then a voltage is applied to the electrodes arranged along the surfaces of between the two opposing substrates thereby to transport the liquid (for example, Pollack et al., "Electrowetting-based actuation of liquid droplets for microfluidic applications", Applied Physics Letters, Vol. 77, No. 11, Pp. 1725-1726, 2000, and Fowler et al., "ENHANCEMENT OF MIXING BY DROPLET-BASED MICROFLUIDICS", IEEE 15th Int. Conf. MEMS January 2002, P. 97-100). A device consisting of two opposing substrates will be referred to as a "device for transporting liquid". In this method, typically, along a liquid-transporting passage to transport liquids, multiple electrodes are formed on one of the two substrates, and one electrode coupled to the ground is provided on another substrate. If a voltage is applied to one of the electrodes underneath a granular liquid, due to the electrowetting phenomenon (for example, Vallet et al., "Electrowetting of water and aqueous solutions on poly(ethylene terephthalate) insulating films", Polymer 37 (1996) 2465-2470) the wettability on the electrode to which the voltage is applied becomes excellent so that the granular liquid moves as to rest upon the electrode to which the voltage is applied. By repeating this, the liquid is transported.

Moreover, it is reported that liquid is distributed into branches using an array of plurality of branched electrodes, or that liquids are merged in a position where a plurality of conduits meet (for example, JP-A-10-267801). Moreover, it is also reported that one granular liquid is divided (for example, U.S. Pat. No. 6,565,727). Moreover, a system is also reported wherein a sample is transported and the measurement is carried out inside a device for transporting liquid (Srinivasan et al., "CLINICAL DIAGNOSTICS ON HUMAN WHOLE BLOOD, PLASMA, SERUM, URINE, SALIVA, SWEAT, AND TEARS ON A DIGITAL MICROFLUIDIC PLATFORM", Micro Total Analysis Systems 2003 p. 1287-1290).

The advantages of these devices for liquid used for transporting which transport liquid include: that these are unsusceptible to air bubbles, due to the use of a substrate, as compared with the cases of using a container whose periphery is enclosed by walls; and the like. Here, there are reported two types of medium for filling the inside of the device for transporting liquid. One of them is a case where the inside is filled with oil as described in Pollack et al., Applied Physics Letters, Vol. 77, No. 11, Pp. 1725-1726, 2000, another is a case where the inside is filled with air as described in Fowler et al., IEEE 15th Int. Conf. MEMS January 2002, P. 97-100.

On the other hand, as for the method for transporting liquid in an automatic analyzer, it is reported that a segment of water solution is introduced into a conduit to transport, the conduit in which liquid such as a silicone oil being stored (for example, U.S. Pat. No. 3,479,141). Moreover, concerning apparatuses for sucking, dispensing separated liquids, or transporting them in a liquid flow, it is reported that a plurality of sample segments are transported while leaving a mutual space therebetween by means of a segment of air and a segment of immiscible liquid (for example, U.S. Pat. No. 4,259, 291). Moreover, it is also reported that a liquid is enclosed by an oil droplet and is transported by the electrowetting phenomenon (Srinivasan et al., "PROTEIN STAMPING FOR MALDI MASS SPECTROMETRY USING AN ELECTROWETTING-BASED MICROFLUIDIC PLATFORM", Lab-On-a-Chip: Platforms, Devices, and Applications, Conf. 5591, SPIE Optics East, Philadelphia, Oct. 25-28, 2004).

In the case where the inside of the device for transporting liquid is filled with oil, because a granular liquid to be transported is enclosed by oil, there are advantages in that: dirt will not likely adsorb to the surface of the device for transporting liquid: the friction between the liquid and the device for transporting liquid is reduced due to the oil; and the voltage required for moving can be reduced: evaporation of the liquid is prevented: and the like. However, because the bottom face and side face of the device for transporting liquid need to be sealed such that the oil will not leak therethrough, it takes time and efforts to mount. Moreover, a problem can be conceived in that when manipulating liquid, a flow occurs in oil, thereby giving affect to other liquids. For example, problems can be conceived in: that when introducing liquid into the device for transporting liquid, a probe for dispensing liquid, and the introduced granular liquids generate a flow in the oil, thereby moving another liquid arranged in the device for transporting liquid: and the like. In the case where liquid moves out of control, it is very likely that the liquid come in contact with other liquids to mix, or that the liquid moves away from a liquid-transporting passage, and thus the transporting may not be possible. Especially, in systems for analyzing, with respect to multiple samples and reagents, a plurality of manipulations such as dispensing, transporting, mixing, detecting, and draining need to be carried out to a plurality of liquids. For this reason, it is essential that the manipulations with respect to a certain liquid does not give effect to other liquids.

Moreover, considering an application to a system for analyzing wherein the measurement is carried out in the device for transporting liquid, a problem can be conceived in that if air bubbles come into oil from a liquid introducing port, the air bubbles will prevent the measurement in the measurement section, and so on. On the other hand, in the case where the inside of the device for transporting liquid is filled with air, there are advantages in that because the bottom face and side face of the device for transporting liquid do not need to be sealed, the mounting will be easy, and that because the periphery of liquid is filled with air, the manipulation to a certain liquid will not give effect to other liquids and an independent and stable manipulation can be carried out to a plurality of liquids. However, unlike the case where the liquid is enclosed by oil, the liquid is in contact directly with the surface of the device for transporting liquid, therefore, problems can be conceived in that the ingredient inside the liquid will likely adsorb; that the voltage required for moving is high because the friction between the liquid and the device for transporting liquid is high; that the evaporation of the liquid cannot be prevented; and the like. In the system for analyzing which uses the device for transporting liquid, in order to measure the concentration of an ingredient inside a sample, the sample being the liquid to be transported, it is essential to prevent the adsorption and evaporation of the ingredient inside the liquid.

In a scheme, wherein a liquid to be transported is enclosed by a droplet of liquid used for transporting, which will not mix with the liquid to be transported, and the liquid used for transporting is transported together with the liquid to be transported, the enclosing with the liquid used for transporting needs to be carried out adequately. Moreover, in an ordinary system for analyzing it is necessary to measure multiple samples sequentially, therefore, at the time of measuring multiple samples in this transporting scheme, the enclosing concerned needs to be carried out adequately and simply in order to prevent the contamination of the sample and improve the throughput of the measurement.

SUMMARY OF THE INVENTION

It is an object of the present invention to provide a device for transporting liquid which has both features in a case of being filled with oil and in a case of being filled with air, and which is easily mounted, and which stably transports a plurality of liquids, wherein the ingredient inside the liquid will not likely adsorb and the voltage required for moving can be reduced, and furthermore the evaporation of samples can be prevented. It is a further object of the invention to provide a system for analyzing wherein multiple samples are transported together with the liquid used for transporting sequentially.

Liquid to be transported is enclosed by a fractionated liquid used for transporting and the liquid used for transporting is transported together with the liquid to be transported. Accordingly, there is provided a device for transporting liquid which is easily mounted and which stably transports a plurality of liquids, wherein the ingredient inside the liquid will not likely adsorb and the voltage required for moving can be reduced, and moreover the evaporation of the sample can be prevented. There is further provided an system for analyzing wherein the liquid to be transported is introduced sequentially into a fractionated liquid used for transporting, which will not mix with the liquid to be transported, and the liquid used for transporting is then transported sequentially together with the liquid to be transported.

One example of the system for analyzing comprises: a first unit including a means for supplying a first liquid, and a means for supplying a second liquid; a second unit including an introducing section into which the first liquid is introduced from the means for supplying the first liquid, a drain section for draining the first liquid, a liquid-transporting passage which is provided with a plurality of electrodes and which joints the introducing section and the drain section, a measurement section provided in at least a part of the liquid-transporting passage, and a voltage application means for applying a voltage to at least a part of the plurality of electrodes; a third unit including a detection system for detecting the measurement section; and a fourth unit for draining liquid from the drain section. The second liquid is immiscible with the first liquid, and the first unit fractionates the second liquid such that the second liquid contains a fractionated first liquid and supplies this to the second unit. The voltage application means applies a voltage to at least a part of the plurality of electrodes as to move along the liquid-transporting passage a compound of the fractured first liquid and second liquid, the compound containing the fractured first liquid and being fractionated.

Another example of the system for analyzing, comprises: a first unit including a means for supplying a first liquid, and a means for supplying a second liquid; a second unit including a first introducing section into which the first liquid is introduced from the means for supplying the first liquid, a second introducing section into which the second liquid is introduced from the means for supplying the second liquid, a drain section for draining the first liquid, a liquid-transporting passage which is provided with a plurality of electrodes and which joints the first introducing section and the drain section, a measurement section provided in at least a part of the liquid-transporting passage, and a voltage application means for applying a voltage to at least a part of the plurality of electrodes; a third unit including a detection system which is arranged adjacent to the measurement section; and a fourth unit for draining liquid from the drain section. The second liquid is immiscible with the first liquid, and the means for supplying the first liquid discharges the first liquid as to fractionate the same, and the means for supplying the second liquid discharges the second liquid as to fractionate the same. The voltage application means applies a voltage to at least a part of the plurality of electrodes so as to move the first liquid from the first introducing section to the second introducing section along the liquid-transporting passage, the first liquid being fractured by the means for supplying the first liquid, and also as to move the first liquid along the liquid-transporting passage, the first liquid being contained by at least a part of the second liquid which is introduced into the second introducing section.

According to the present invention, the mounting is simpler as compared with the conventional device for transporting liquid which is filled with oil, and a stable and independent manipulation can be carried out to a plurality of liquids, and the liquid will not move out of control due to an oil flow generated by the manipulations of liquid, such as dispensing, transporting, or the like. Moreover, the liquid enclosed by a fractionated oil droplet can be introduced sequentially into the device for transporting liquid, and the throughput of the system for analyzing which treats a plurality of samples can be increased.

Other objects, features and advantages of the invention will become apparent from the following description of the embodiments of the invention taken in conjunction with the accompanying drawings.

DETAILED DESCRIPTION OF THE INVENTION

Embodiment 1

Figure 1:
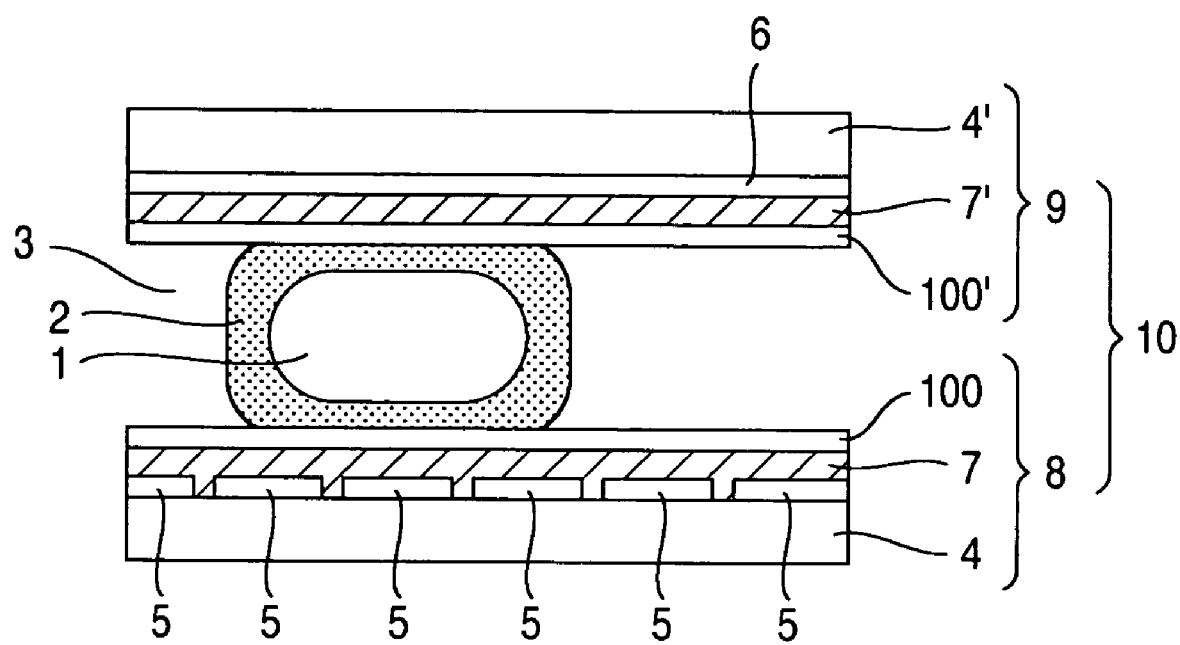
FIG. 1 is a view showing a cross section of a liquid-transporting passage of a device for transporting liquid in an embodiment 1 of the present invention.

This example shows a procedure, wherein an oil droplet is used as a droplet for liquid used for transporting in a device for transporting liquid to thereby transport the liquid enclosed by the oil droplet. FIG. 1 shows a cross sectional configuration in a liquid-transporting passage of a device for transporting liquid 10 in this example. The device for transporting liquid 10 comprises a lower substrate 8 and an upper substrate 9. In the lower substrate 8, multiple control electrodes 5 are arranged along the transporting direction of a liquid (droplet) 1 in the upper surface of an insulating substrate 4, and moreover the surface thereof is covered with an insulating film 7. In the upper substrate 9, one common electrode 6 is arranged in the lower surface of an insulating substrate 4', and the surface thereof is covered with an insulating film 7'. Furthermore, in the surfaces of the respective insulating films 7 and 7', water-repellent films 100, 100' are applied to the surfaces in order to give water repellence thereto such that the liquid may be transported easily. In between these two substrates, the liquid 1 to be transported is placed and the periphery thereof is enclosed by an oil droplet 2. That is, the droplet of the liquid 1 to be transported is contained by the oil droplet 2, providing for a compound of the liquid 1 droplet and the oil droplet 2. Here, "contain" implies that one oil droplet is located as to cover substantially the outer surface of one liquid (droplet). There exists air 3 around the oil droplet 2.

In this example, a quartz is used for the insulating substrates 4 and 4', ITO (Indium-Tin Oxide) for a control electrode 5 and a common electrode 6, $SiO_2$ deposited with CVD (Chemical Vapor Deposition) for the insulating films 7, 7', and CYTOP (registered trademark) made by Asahi Glass Co., Ltd is used as a water-repellent film. The thickness of ITO is set to 70 nm and the thickness of the insulating film 7 formed with CVD is set to 200 nm. Moreover, the distance between the lower substrate 8 and the upper substrate 9 is set to 0.5 mm. Moreover, a solution of 0.9 wt % NaCl is used as the liquid 1, a silicone oil as the oil droplet 2, and the liquid volume is set to 5 µL, respectively. By placing the liquid enclosed by the oil droplet 2 in between the lower substrate 8 and the upper substrate 9, an anti-evaporation effect of the oil is increased and at the same time it is possible to prevent the oil from being gravitated and separated from the liquid.

FIG. 2 shows perspective views, when seen from above, of the device for transporting liquid used in the example. For simplicity and clarity, in the present application, in the perspective views of FIG. 2, and FIG. 8 through FIG. 15, only the liquid 1, the oil droplet 2, and the control electrode 5 are illustrated, and the control electrode to which a voltage is currently applied is shown by hatching. Moreover, a common electrode 6 located above the control electrode 5 is coupled to the earth, and a voltage is applied to between the common electrode 6 and a part of the control electrode 5. Moreover, in the present application, the control electrode 5, to which a voltage is not currently applied, is made floating (i.e., the control electrode 5 is not coupled to anywhere), and when turning off the applied voltage the application of the voltage is stopped, and then the control electrode 5 is coupled to the earth once, and thereafter the control electrode 5 is made floating. Accordingly, the insulating film and water-repellent film on the control electrode can be prevented from remaining partially charged when turning off the applied voltage. If a voltage is applied to between the common electrode 6 and the control electrode 5, the liquid 1 having a region, the region partially overlapping the control electrode 5 when seen from above, will move as to rest upon the control electrode 5 to which a voltage is currently applied, namely, the liquid moves as to rest upon the control electrode 5 to which a voltage is currently applied. First, as shown in FIG. 2A, a plurality of control electrodes 5 are arranged along the liquid-transporting passage, and when the liquid 1 enclosed by the oil droplet 2 exists near the control electrode 5b, if a voltage is applied to the control electrode 5b, then the liquid 1 will move as to rest upon the control electrode 5b, as shown in FIG. 2B.

Figure 2A:
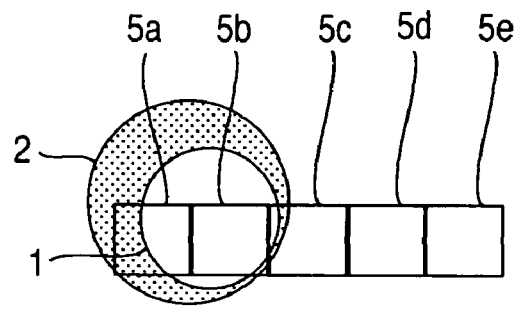
FIG. 2A is a schematic view explaining a procedure for transporting liquid in the embodiment 1 of the invention.
Figure 2B:
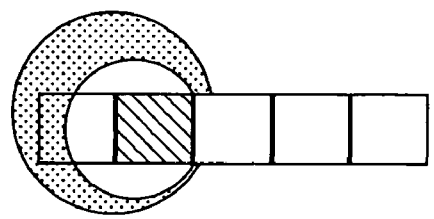
FIG. 2B is a schematic view explaining the procedure for transporting liquid in the embodiment 1 of the invention.
Figure 2C:
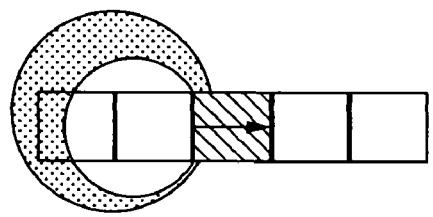
FIG. 2C is a schematic view explaining the procedure for transporting liquid in the embodiment 1 of the invention.
Figure 2D:
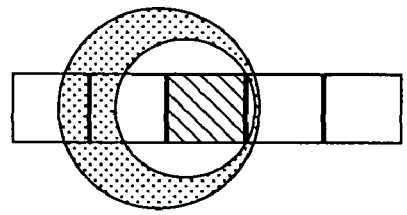
FIG. 2D is a schematic view explaining the procedure for transporting liquid in the embodiment 1 of the invention.
Figure 2E:
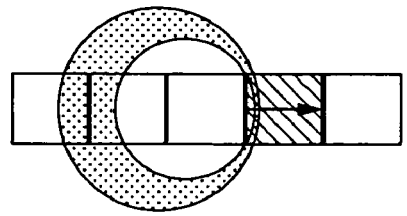
FIG. 2E is a schematic view explaining the procedure for transporting liquid in the embodiment 1 of the invention.
Figure 2F:
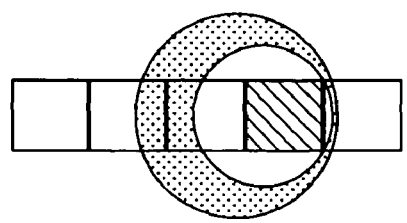
FIG. 2F is a schematic view explaining the procedure for transporting liquid in the embodiment 1 of the invention.

Next, if a voltage is applied to a control electrode 5c and the applied voltage to the control electrode 5b is turned off, then, as shown in FIG. 2C, after coming in contact with a gas-liquid interface of between the oil droplet 2 and the air 3, the liquid 1 will move together with the oil droplet 2 while pushing the gas-liquid interface of between the oil droplet 2 and the air 3, as shown in FIG. 2D, and it will move as to rest upon the control electrode 5c. Furthermore, if a voltage is applied to a control electrode 5d and the applied voltage to the control electrode 5c is turned off, then, as shown in FIG. 2E, the liquid 1 will move together with the oil droplet 2 while pushing the gas-liquid interface of between the oil droplet 2 and the air 3, as shown in FIG. 2F, and it will move as to rest upon the control electrode 5d. By repeating this, it is possible to transport the liquid 1 while being enclosed by the oil droplet 2. Moreover, the liquid 1 enclosed by the oil droplet 2 will move along an array of the control electrodes. By enclosing liquid with a liquid used for transporting like in this example, the adsorption of the ingredient inside the liquid to be transported, i.e., the adsorption to the substrate surface, can be prevented, and the evaporation of the liquid can be also prevented. Moreover, because the friction between the liquid 1 and the device for transporting liquid 10 is small, the liquid can be transported even with a low voltage as compared with a case where the inside of the device for transporting liquid is filled with air. Lowering the voltage is useful because the insulating film may be destroyed if the voltage applied to the control electrode is too high. Moreover, because the liquid used for transporting is fractionated and separated as the oil droplet 2, an oil flow generated by transporting the liquid 1 will not transmit to other liquids, and thus a plurality of liquids in the device for transporting liquid can be manipulated stably and independently.

Although in this example a solution of NaCl was used as the liquid 1, even a pure water, and an ionic liquid such as a buffer solution may be used. Moreover, blood, and a DNA-containing solution may be used. Moreover, the liquid may contain a latex particle, a cell, a magnetic bead, or the like Moreover, although a silicon oil was used as the oil droplet 2, a liquid, such as a vegetable oil, a paraffin oil, a fluorine oil such as Krytox (registered trademark) made by DuPont Co. Ltd., and a fluorine solvent, which will not mix with the liquid to be transported, i.e., an immiscible liquid may be used. Moreover, although a quartz was used as the insulating substrates 4 and 4', a substrate wherein an insulating film such as an oxide film is deposited on a conductive substrate such as Si, or a resin substrate may be used. Moreover, although $SiO_2$ deposited with CVD was used for the insulating films 7 and 7', an insulating film, such as poly silazane, SiN, or Parylene may be used. Although CYTOP made by Asahi Glass Co. Ltd. was used as water-repellent films 100, 100', TeflonAF (registered trademark) made by DuPont Co. Ltd., a water-repellent film made of a silicone system, and a CF film (Fluorocarbon film) deposited with CVD, may be used.

Figure 3:
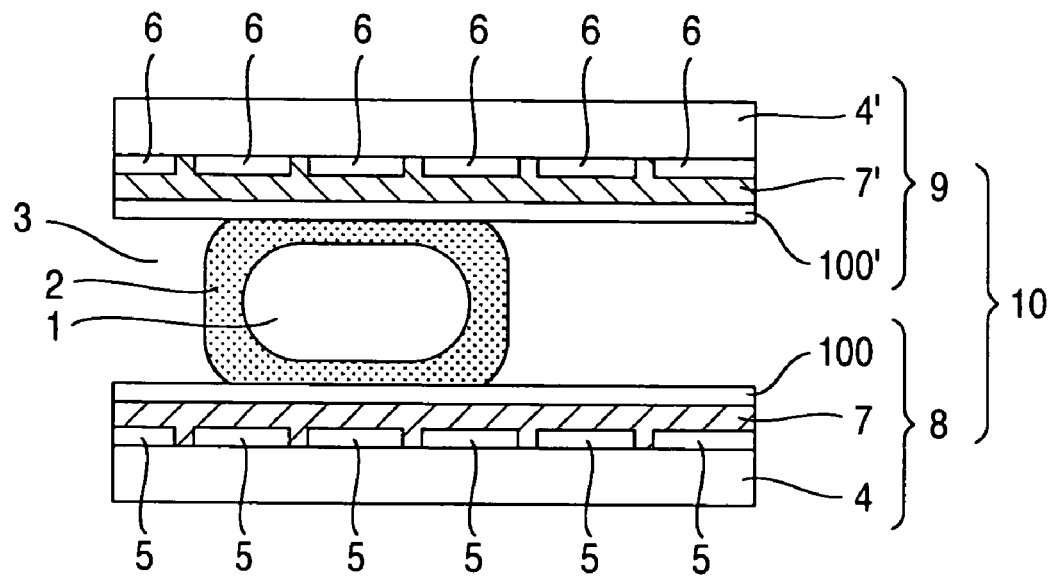
FIG. 3 is a view showing a cross section of a liquid-transporting passage of another configuration in the embodiment 1 of the invention.
Figure 4:
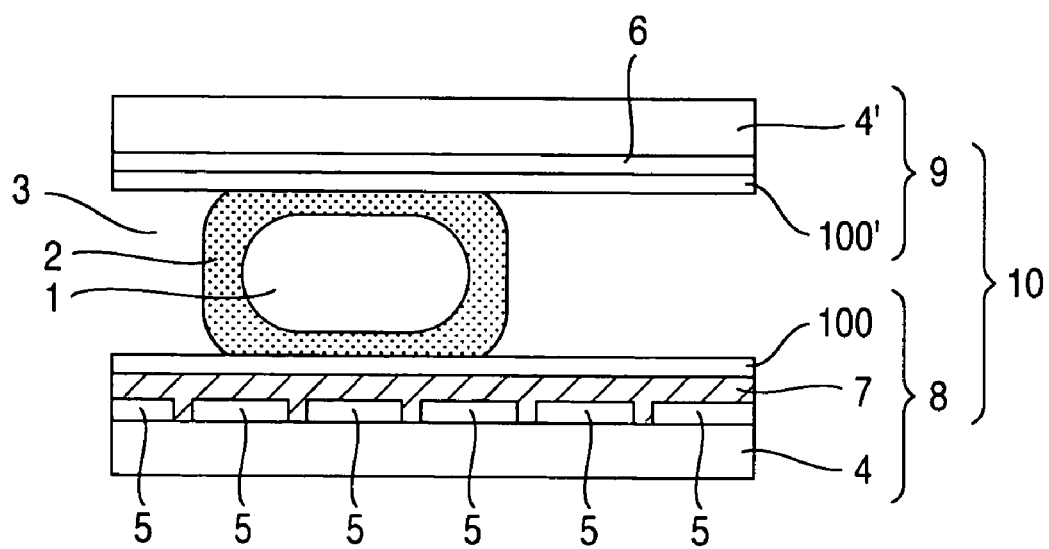
FIG. 4 is a view showing a cross section of a liquid-transporting passage of another configuration in the embodiment 1 of the invention.

Moreover, in this example, although a water-repellent film was deposited on the insulating film, a water-repellent insulating film or an insulating water-repellent film may be used. In this case, the device fabrication will be simplified because the number of process steps is reduced. Moreover, in this example, although the number of the common electrode 6 was set to one, a plurality of common electrodes 6 may be arranged in the upper substrate 9, as shown in FIG. 3. In this case, there is an advantage in increasing the positional accuracy of the liquid during the transportation. Moreover, although in this example the control electrode 5 and the common electrode 6 are covered with the insulating films 7 and 7', respectively, it is also possible that the surface of the control electrode 5 is covered with the insulating film 7 while the insulating film 7' does not exist in the surface of the common electrode 6, as shown in FIG. 4. In this case, the configuration can be simplified. Furthermore, the surface of the common electrode 6 may not be coated with the water-repellent films 100, 100'. In this case, the configuration can be simplified further.

Figure 5:
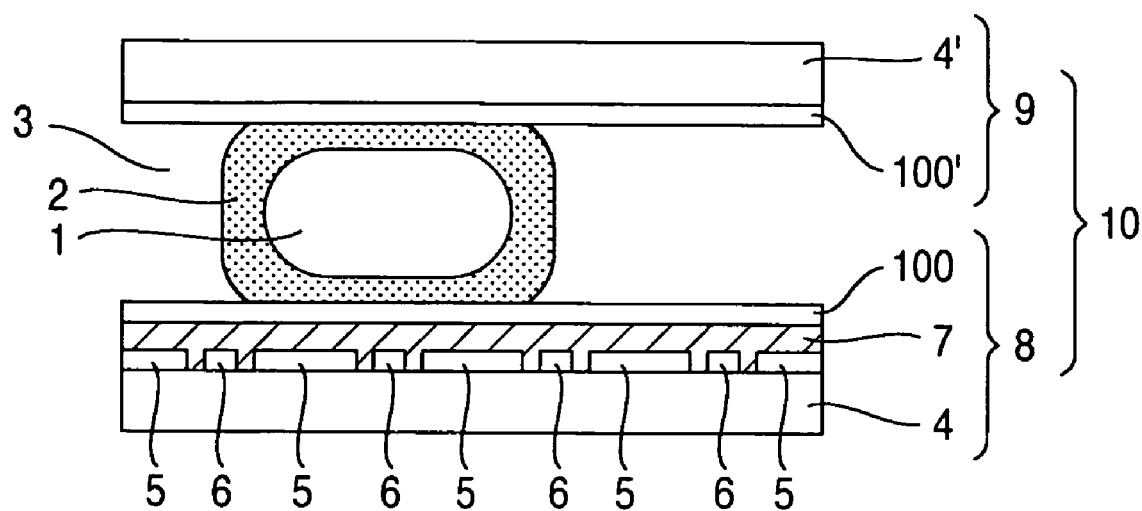
FIG. 5 is a view showing a cross section of a liquid-transporting passage of another configuration in the embodiment 1 of the invention.
Figure 6:
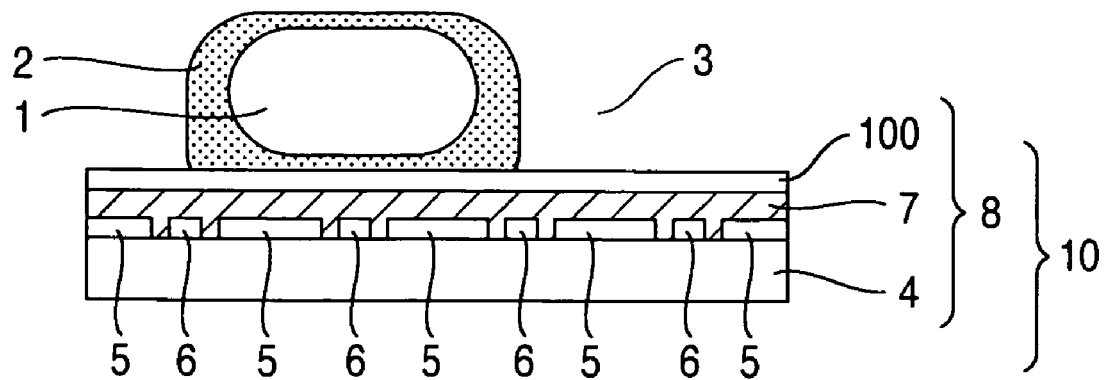
FIG. 6 is a view showing a cross section of a liquid-transporting passage of another configuration in the embodiment 1 of the invention.

Moreover, as shown in FIG. 5, it is also possible that the common electrode 6 is not arranged in the surface of the upper substrate 9 while a plurality of electrodes are provided in the lower substrate 8, wherein any one of these plurality of electrodes is the control electrode 5, and any another one is the common electrode 6. For example, the common electrodes 6 are arranged in between the control electrodes 5 of the lower substrate 8. In this case, because it is not necessary to deposit an electrode in the upper substrate, the configuration will be simplified. Furthermore, the surface of the insulating substrate 4' in the upper substrate 9 may not be coated with a water-repellent film. In this case, the configuration can be simplified further. Moreover, as shown in FIG. 6, the transporting can be carried out even in a configuration wherein the upper substrate 9 is not provided and there is only the lower substrate 8. In this case, the configuration will be simplified further.

Moreover, although in this example the lower substrate 8 and upper substrate 9 constituting the device for transporting liquid 10 are arranged horizontally, a part of the lower substrate 8 and upper substrate 9, or the whole of them may be arranged with an angle relative to the horizontal direction. In the conventional device for transporting liquid which is filled with oil, the oil might leak if an angle is given to the horizontal direction, however, according to the present invention, because the oil is kept by two substrates, the oil will unlikely be mobilized and thus an angle can be given to relative to the horizontal direction. If an angle can be given relative to the horizontal direction, the area for installing the whole apparatus can be reduced, which is useful. Moreover, although in this example the periphery of the liquid 1 is enclosed by a silicone oil, the periphery of the silicone oil may be enclosed further by a fluorine oil or a fluorine solvent.

Figure 7:
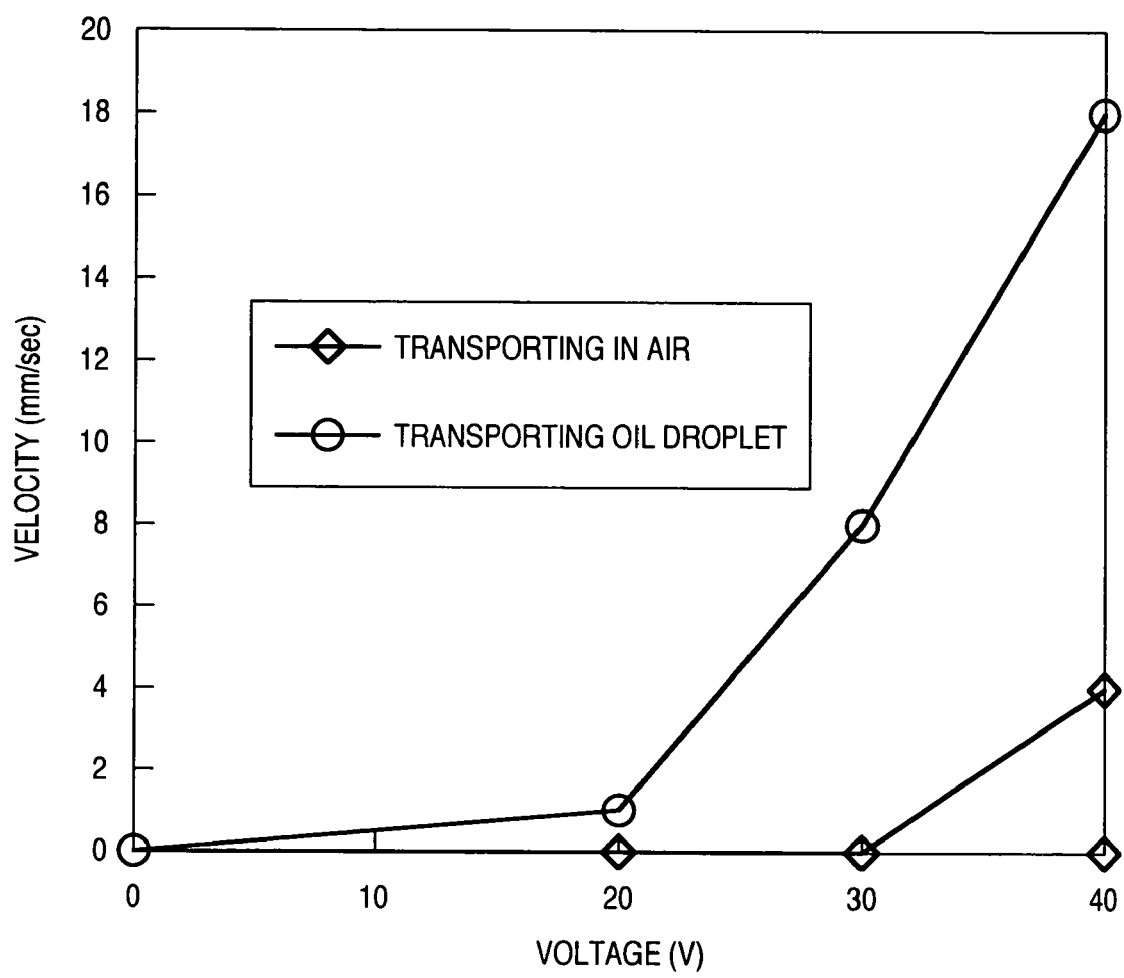
FIG. 7 is a view showing a comparison of the velocities in the devices for transporting liquid in the invention.

Next, the velocity of transporting an oil droplet in the case where the liquid 1 enclosed by the oil droplet 2 is transported while pushing the gas-liquid interface of the oil droplet 2, is compared with the velocity of transporting in air in the case where there exists air around the liquid 1. FIG. 7 shows the velocity variation of the liquid 1 against the voltage variation for each case. In case of transporting the oil droplet, the liquid can be transported from 20V, while in case of transporting in air, the liquid cannot be transported at 20V, and instead can be transported from 40V. It is thus apparent that the voltage required for transporting can be reduced. This is due to the fact that the oil penetrates between the liquid 1 and the surface of the device for transporting liquid, thereby alleviating the friction. Because the insulating film may be destroyed if the voltage applied to the electrode is too high, the reduction of the voltage for transporting the liquid is useful.

Figure 8A:
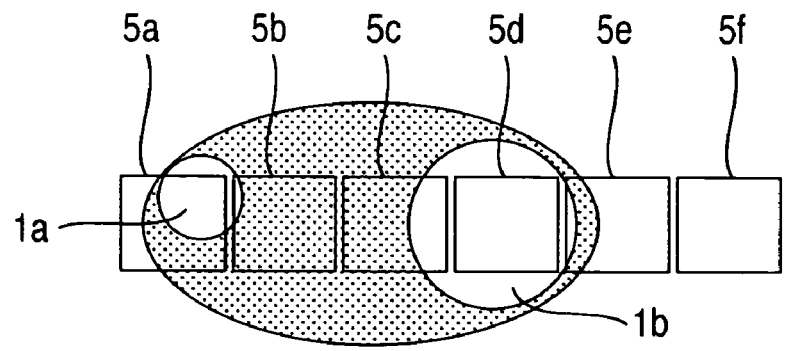
FIG. 8A is an explanatory view of transporting liquid together with a substance existing in oil in the embodiment 1 of the invention.
Figure 8B:
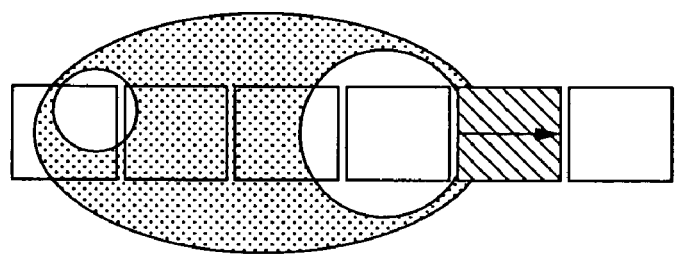
FIG. 8B is an explanatory view concerning the transporting of a liquid including a substance existing in oil in the embodiment 1 of the invention.
Figure 8C:
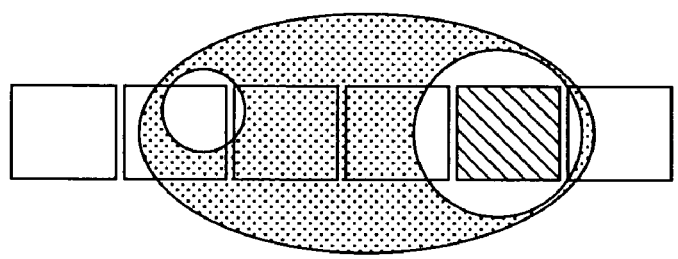
FIG. 8C is an explanatory view concerning the transporting of a liquid including a substance existing in oil in the embodiment 1 of the invention.
Figure 8D:
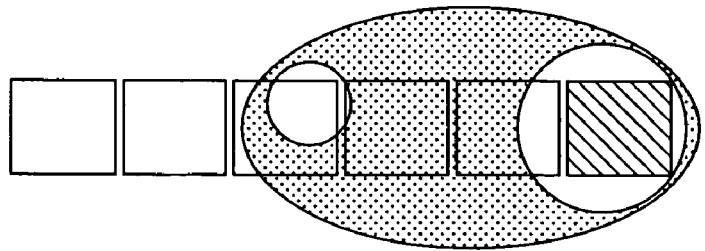
FIG. 8D is an explanatory view concerning the transporting of a liquid including a substance existing in oil in the embodiment 1 of the invention.

Moreover, the case, in which a substance contained in the oil droplet is transported at the same time as the liquid is, will be described using FIG. 8. As shown in FIG. 8A, when two liquids (hereinafter, referred to as a "droplet") 1a and 1b exist within one oil droplet 2 in the liquid-transporting passage, if a voltage is applied to a control electrode 5e, as shown in FIG. 8B, then only liquid 1b having an overlapping with the control electrode 5e will move onto the control electrode 5e. At this time, the liquid 1a is pushed by the gas-liquid interface between the oil of the oil droplet 2 and the air, and is transported together with the liquid 1b as shown in FIG. 8C. Moreover, if a voltage is applied to a control electrode 5f and the applied voltage of the control electrode 5e is turned off as shown in FIG. 8D, the liquid 1b moves onto the control electrode 5f and at the same time the liquid 1a also moves while being pushed by the gas-liquid interface between the oil and the air. Similar move can be carried out also when two or more liquids exist within the oil droplet. In this way, in the case where a plurality of liquids (droplets) exit within the oil droplet 2, the droplets other than the droplet to which a voltage is applied can move together while being pushed by the gas-liquid interface of the oil droplet. Accordingly, even in case of transporting two or more liquids simultaneously, by enclosing them with the same oil droplet only one liquid just needs to be controlled, which will simplifies the control of liquid.

Although in this example, liquid other than the liquid to which a voltage is applied is taken as an example as a substance within the oil droplet 2, the substance just needs to be a substance contained in the oil droplet 2, and even a solid such as a particle can move in the same manner. Usually, oil can not be controlled to transport in the device for transporting liquid, however, according to the present invention, by transporting liquid which is contained in the oil, the oil can be transported to a predetermined position. Accordingly, by moving and mixing a plurality of oils, the substance contained in the oil can be even reacted.

Embodiment 2

Figure 9A:
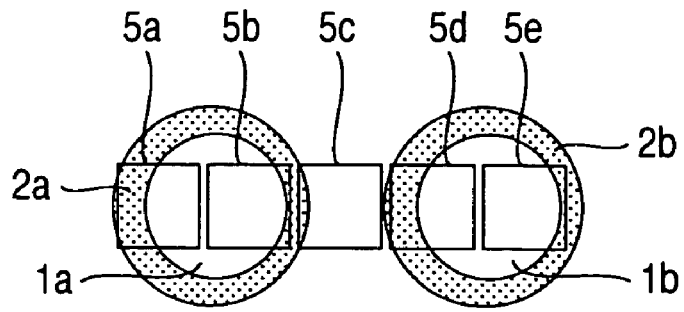
FIG. 9A is a schematic view explaining an embodiment 2 of the invention.
Figure 9B:
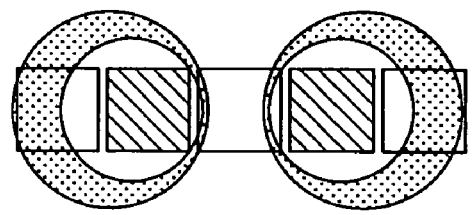
FIG. 9B is a schematic view explaining the embodiment 2 of the invention.
Figure 9C:
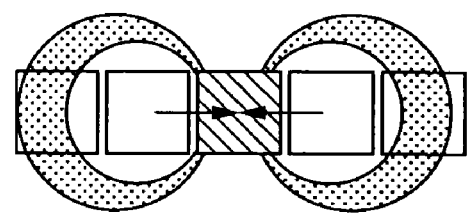
FIG. 9C is a schematic view explaining the embodiment 2 of the invention.
Figure 9D:
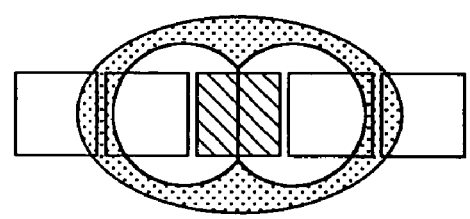
FIG. 9D is a schematic view explaining the embodiment 2 of the invention.
Figure 9E:
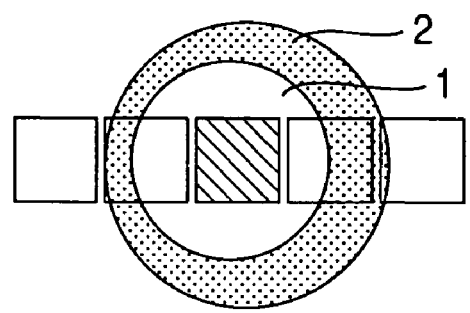
FIG. 9E is a schematic view explaining the embodiment 2 of the invention.

This example shows a procedure wherein mixing or the like of two liquids enclosed by the oil droplet 2 is carries out. The mixing procedure is divided into combining and stirring to be described hereinafter. When a liquid (droplet) 1a enclosed by an oil droplet 2a and a liquid 1b enclosed by an oil droplet 2b are placed on the control electrode 5 as shown in FIG. 9A, if a voltage is applied to control electrodes 5b and 5d which are located in between the two liquids (droplets), and on which a part of the respective droplets overlap, respectively, the liquids (droplets) 1a and 1b will move as to rest upon the control electrode which the respective part thereof overlapped, as shown in FIG. 9B. Then, a voltage is applied to a control electrode 5c, which is the control electrode arranged in between the two liquids (droplets) as shown in FIG. 9C, the control electrode 5c being arranged in between the control electrodes 5b and 5d, the control electrode 5c being the destination of the move of the two liquids (droplets), and then the voltage applied to the control electrodes 5b and 5d, which are adjacent to the control electrode 5c, is turned off. Accordingly, the droplets of the two liquids attempt to move onto the control electrode 5c, and thus the oil 2a and oil 2b are combined as shown in FIG. 9D, and thereafter the liquid 1a and liquid 1b are combined to be the liquid 1 enclosed by one oil as shown in FIG. 9E. Because the liquids to be combined are enclosed by an oil droplet like in this example, a plurality of liquids in the device for transporting liquid can be manipulated stably and independently without transmitting to liquids other than the liquid to be combined an oil flow generated by the combining.

Figure 10:
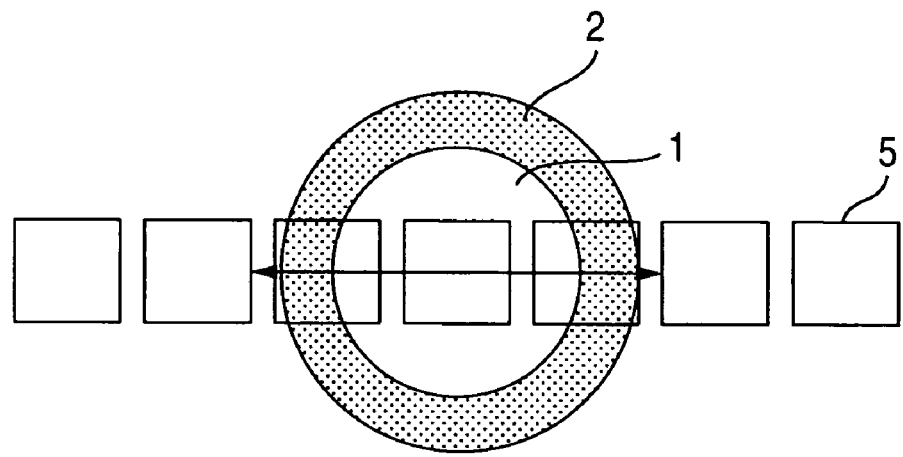
FIG. 10 is a schematic view explaining the embodiment 2 of the invention.
Figure 11:
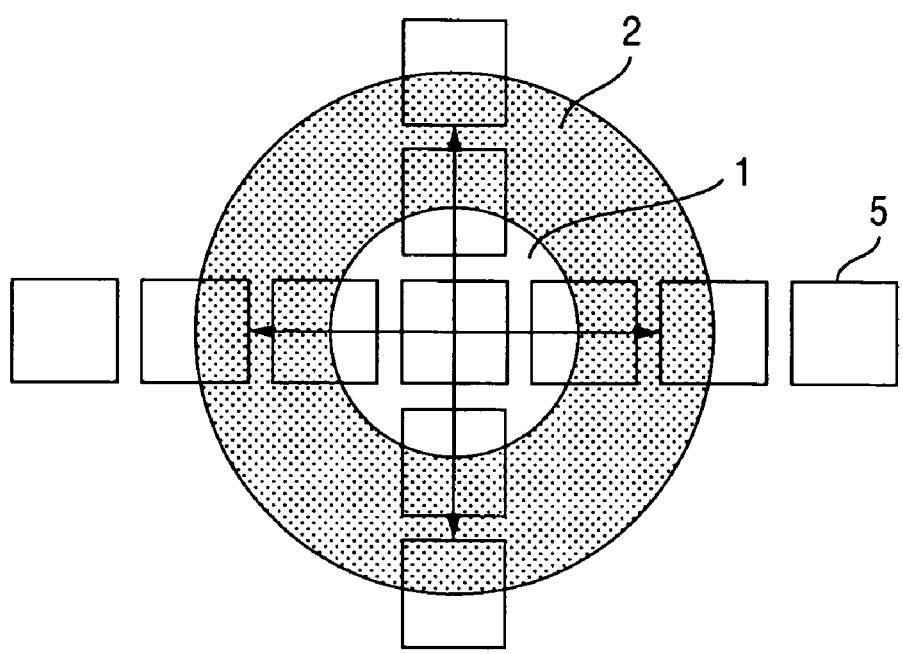
FIG. 11 is a schematic view explaining the embodiment 2 of the invention.
Figure 12:
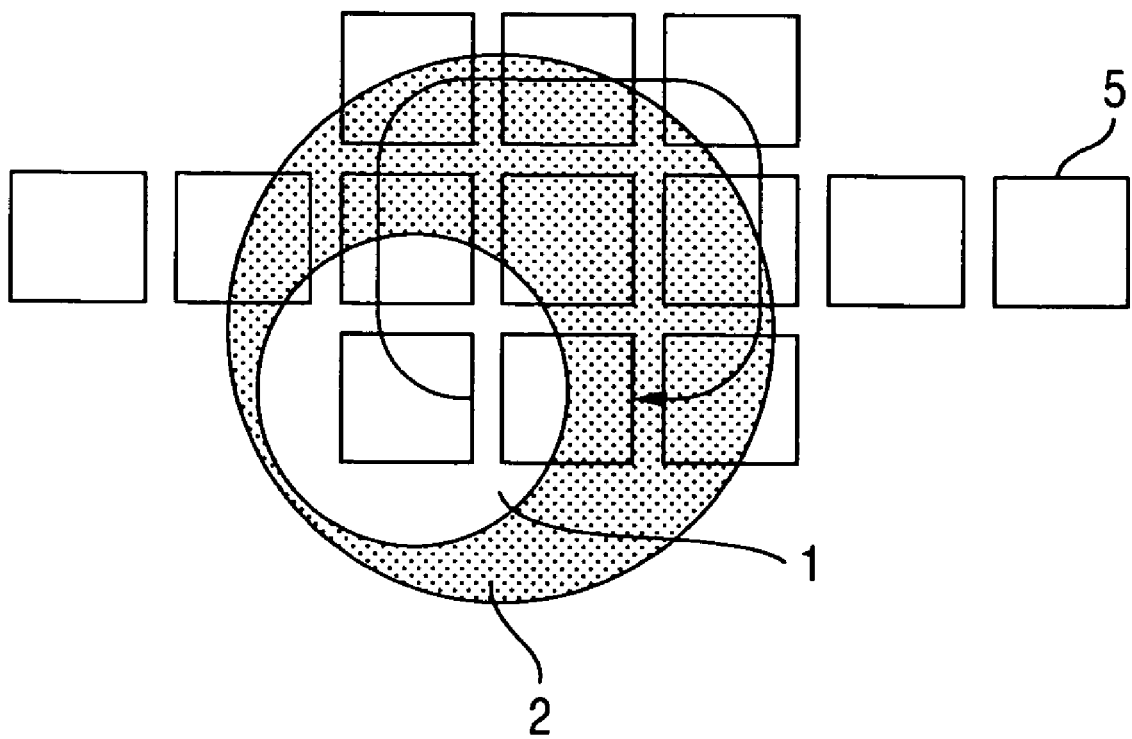
FIG. 12 is a schematic view explaining the embodiment 2 of the invention.

Next, there is shown a procedure for stirring the ingredient of a liquid enclosed by an oil droplet. FIG. 10 shows a layout view of control electrodes to stir the liquid 1. When the liquid 1 within the oil droplet 2 is located on a plurality of control electrodes (shown as a square in the view), which are arranged in a substantially straight line as shown in FIG. 10, a voltage is applied to the control electrode 5 sequentially to reciprocate the liquid 1, and thereby the internal ingredient can be stirred. Moreover, as shown in FIG. 11, the control electrodes are arranged on a plurality of substantially straight lines, whose directions differ, and also the substantially straight lines concerned are crossed to reciprocate the liquid 1 in two different directions repeatedly, and thereby the internal ingredient can be stirred. In this case, because the liquid is transported in different directions, a part of the liquid will deform to facilitate the diffusion. Moreover, as shown in FIG. 12, by applying a voltage to the control electrodes along the moving direction of the liquid 1 on the control electrodes arranged in a two-dimensional array, the moving direction of the liquid 1 can be controlled two-dimensionally to stir. For example, by moving the liquid 1 like drawing a circle, the liquid 1 can be also stirred. In this case, while the liquid moves drawing a circle, each part of the liquid will deform to facilitate the diffusion. Moreover, at this time, if the size of the oil droplet 2 is large, then the liquid 1 can move in the oil droplet without contacting to the gas-liquid interface between the oil and gas, and thereby the stirring can be carried out more quickly.

Due to the fact that like in this example the liquid to stir is enclosed by an oil droplet, even if the liquid moves to stir, an oil flow generated accordingly will not transmit to other liquids, therefore, the liquids other than the liquid currently being stirred can be controlled stably. As described above, by carrying out a mixed manipulation of combining and stirring in the oil droplet, a plurality of liquids in the device for transporting liquid can be manipulated stably and independently without transmitting to other liquids an oil flow generated by the mixed manipulation. Such a mixed manipulation is important in analysis. For example, in order to measure TP (Total Protein) item, which is a biochemical analysis item for measuring the total amount of protein contained in blood, a 1 μL of blood as a sample and a 10 μL of autosera TP reagent made by Daiichi Pure Chemicals Co., Ltd. as a reagent, are mixed, and then the absorbancy after 10 minutes is measured to determine TP.

Embodiment 3

This example shows a procedure for separating one liquid 1 enclosed by the oil droplet 2 into two liquids 1 enclosed by the oil droplet 2.

Figure 13A:
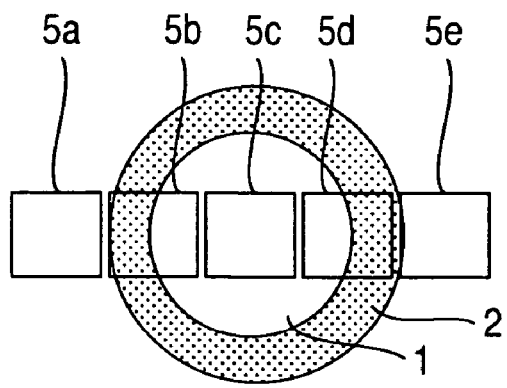
FIG. 13A is a schematic view explaining an embodiment 3 of the invention.
Figure 13B:
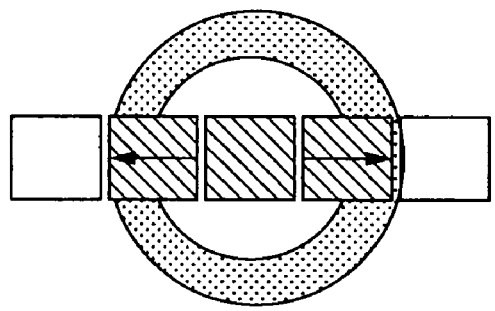
FIG. 13B is a schematic view explaining the embodiment 3 of the invention.
Figure 13C:
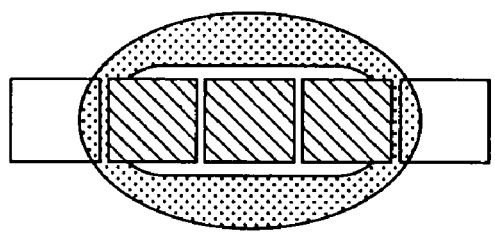
FIG. 13C is a schematic view explaining the embodiment 3 of the invention.
Figure 13D:
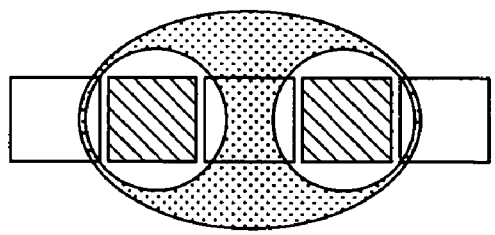
FIG. 13D is a schematic view explaining the embodiment 3 of the invention.
Figure 13E:
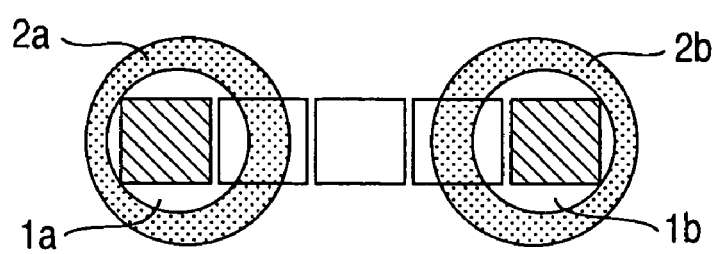
FIG. 13E is a schematic view explaining the embodiment 3 of the invention.

When the liquid 1 enclosed by the oil droplet 2 is placed on the control electrode 5 arranged in a straight line, as shown in FIG. 13A, a voltage is applied simultaneously or substantially simultaneously to the control electrode 5c, which a part of the liquid 1 overlaps and which is also located near the center of the liquid 1, and to the control electrodes 5b and 5d, which are adjacent to the control electrode located near the center of the liquid and are in a symmetrical position relative to the control electrode concerned as shown in FIG. 13B. Then, as shown in FIG. 13C, the liquid will deform wide horizontally. Then, the applied voltage to the control electrode 5c located near the center of the liquid is turned off. This separates the liquid 1 into two liquids (droplets) 1a and 1b, as shown in FIG. 13D. At this time, a voltage is applied to each of the control electrode 5a arranged ahead of the control electrode 5b toward one edge side direction, in a row of control electrodes, and also to the control electrode 5e arranged ahead of the control electrode 5d toward another edge side direction, and as shown in FIG. 13E, by turning off the applied voltages to the control electrodes 5b and 5d, the liquid 1 can be separated into the liquid (droplet) 1a enclosed by the oil droplet 2a and the liquid 1b (droplet) enclosed by the oil droplet 2b. Like this example, by separating the liquid 1 into two liquids in the oil droplet, a plurality of liquids in the device for transporting liquid can be manipulated stably and independently without having influence on liquids other than the liquid to separate, the influence being caused by an oil flow generated by the operation of separating.

Embodiment 4

Figure 14A:
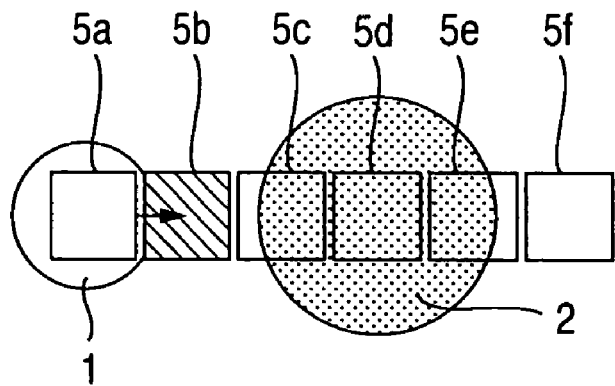
FIG. 14A is a schematic view explaining an embodiment 4 of the invention.
Figure 14B:
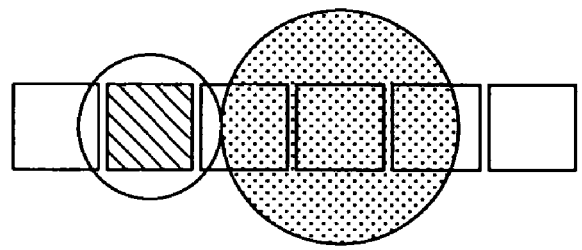
FIG. 14B is a schematic view explaining the embodiment 4 of the invention.
Figure 14C:
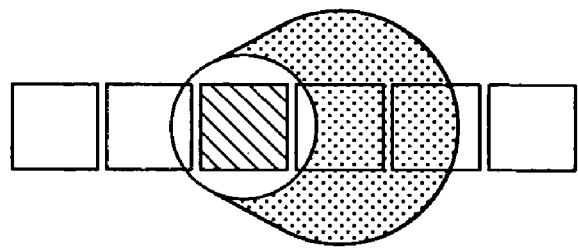
FIG. 14C is a schematic view explaining the embodiment 4 of the invention.
Figure 14D:
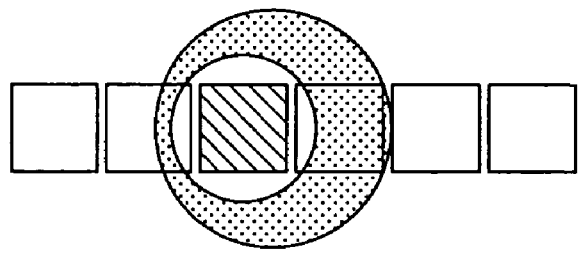
FIG. 14D is a schematic view explaining the embodiment 4 of the invention.

This example shows a procedure for forming a liquid enclosed by an oil droplet in the device for transporting liquid. The liquid 1 and the oil droplet 2 are placed separately on the control electrode 5 arranged in a straight line as shown in FIG. 14A. Here, in a row of a plurality of control electrodes, if a voltage is applied to the control electrode 5b arranged in the direction toward the electrode on which the center of the oil droplet 2 rests, the direction being seen from the electrode on which the center of the liquid 1 rests, then the liquid 1 will move onto the control electrode 5b, as shown in FIG. 14B. Then, as shown in FIG. 14C, a voltage is applied to the control electrode 5c arranged in the direction toward the electrode on which the center of the oil droplet 2 rests, the direction being seen from the control electrode which was the destination of the liquid 1, the control electrode 5c being arranged in the direction toward the electrode on which the center of the liquid 1 rests, the direction being seen from the electrode on which the center of the oil droplet 2 rests, and then the applied voltage to the control electrode 5b is turned off. At this time, after the droplet 1 comes in contact with the oil droplet 2, the oil droplet 2 will move to enclose the whole liquid 1 as shown in FIG. 14D, and thus the liquid 1 enclosed by the oil droplet can be formed. As shown in this example, a liquid enclosed by an oil droplet can be formed easily by transporting the liquid to contact with an oil in the device for transporting liquid. For example, in the case where an analysis is carried out using the device for transporting liquid, there is an advantage in that by separating a sample, like in this example, into multiple liquids in the device for transporting liquid 1, and measuring each of them, multiple items can be measured simultaneously and the throughput can be increased.

Figure 15A:
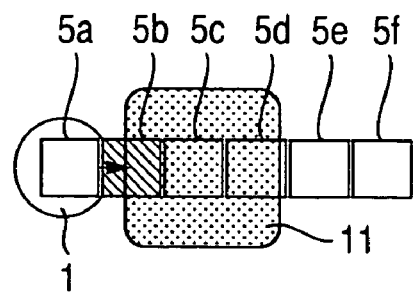
FIG. 15A is a schematic view explaining the embodiment 4 of the invention.
Figure 15B:
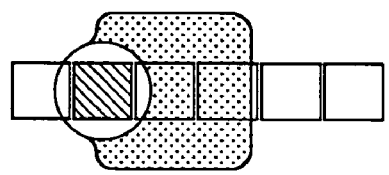
FIG. 15B is a schematic view explaining the embodiment 4 of the invention.
Figure 15C:
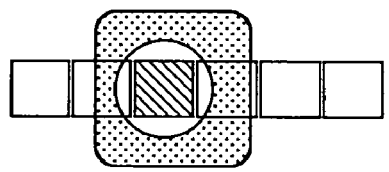
FIG. 15C is a schematic view explaining the embodiment 4 of the invention.
Figure 15D:
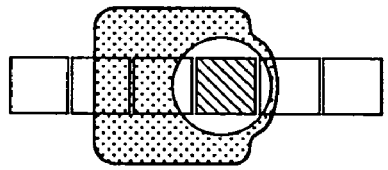
FIG. 15D is a schematic view explaining the embodiment 4 of the invention.

Moreover, there is shown a procedure wherein a liquid (droplet) enclosed by an oil droplet is formed from an oil buffer, which is stored in a part of the device for transporting liquid by means of a physical fence, or due to a hydrophilic or hydrophobic nature of the surface thereof. As shown in FIG. 15A, when the liquid 1 and an oil region 11 formed as an oil reservoir are placed separately on the control electrodes 5a, 5b, 5c, 5d, 5e, and 5f arranged in a substantially straight line, if a voltage is applied to the control electrode 5b, then the liquid 1 will move onto the control electrode 5b as shown in FIG. 15B. At this time, a part of the liquid 1 will overlap a region in which the oil region 11 is located. Then, as shown in FIG. 15C a voltage is applied to the control electrode 5c, and the applied voltage to the control electrode 5b is turned off. Then, the liquid 1 moves to the control electrode 5c to be completely enclosed in the oil region 11, and then, as shown in FIG. 15D, a voltage is applied to the control electrode 5d, and the voltage to the control electrode 5c is turned off. Then, it will move onto the control electrode 5d.

Figure 15E:
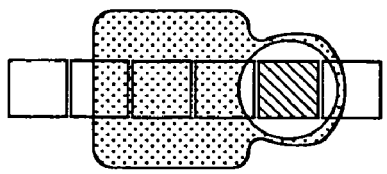
FIG. 15E is a schematic view explaining the embodiment 4 of the invention.
Figure 15F:
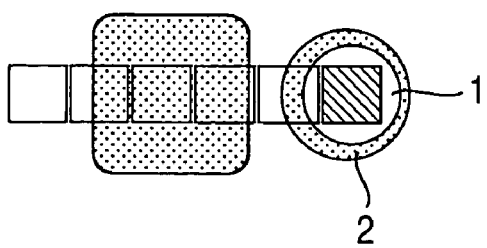
FIG. 15F is a schematic view explaining the embodiment 4 of the invention.

Then, as shown in FIG. 15E, a voltage is applied to a control electrode 5e, and the voltage to the control electrodes 5d is turned off. Then, the liquid 1 will move to the outside of the oil region 11. At this time, a part of the oil is still in contact with the oil region 11, and then a voltage is applied further to the control electrode 5f, as shown in FIG. 15F, and by turning off the voltage to the control electrode 5e, a certain amount of oil can be separated from the oil region 11 to form the liquid 1 enclosed by the oil droplet 2. Moreover, the optimization of the fence of the oil region 11, the hydrophilic and hydrophobic surface states, and the shape of the electrode, or the like, also allows for the oil to be separated from the oil region and to be formed more easily. Like in this example, by transporting and contacting a liquid to an oil region in which oil is stored, a liquid enclosed by oil can be formed easily. Moreover, by transporting liquid to the oil region sequentially, a number of liquids enclosed by oil can be formed using one oil region.

Embodiment 5

In this example, the device for transporting liquid is applied to a system for analyzing, and there is shown a procedure, wherein a sample and a reagent are introduced as a granular liquid, i.e., a droplet, into one region in the device for transporting liquid, respectively, and they are enclosed by an oil droplet, the oil droplet being a liquid used for transporting, and are then transported as a compound droplet composed of an oil droplet and sample, as well as a compound droplet composed of an oil droplet and reagent, etc., and then these compound droplets are combined to serve as a reaction liquid, which is then stirred and detected and thereafter is drained out together with the oil droplet which encloses the periphery thereof.

Figure 16:
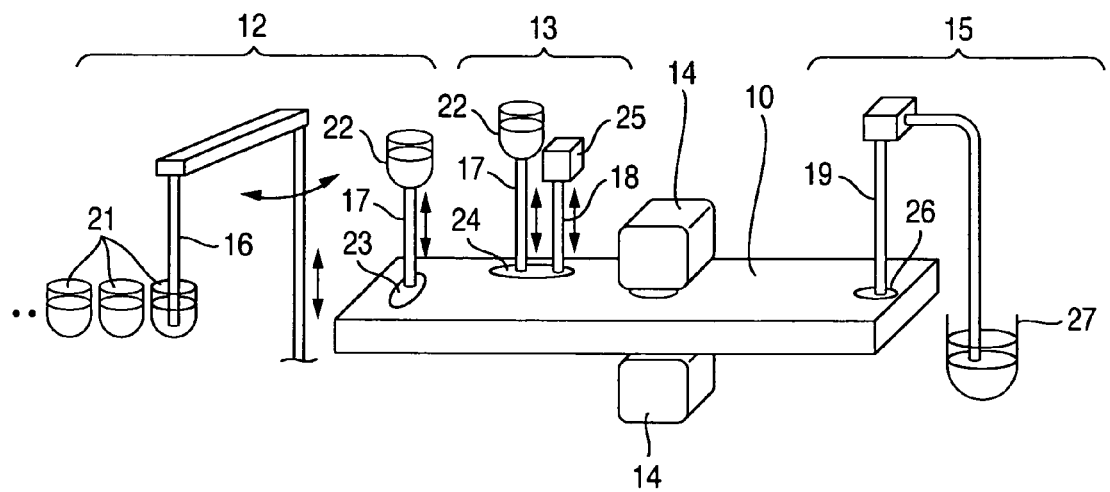
FIG. 16 is a schematic view of a system for analyzing in an embodiment 5 of the invention.

FIG. 16 shows a configuration of the system for analyzing. The system for analyzing comprises: a device for transporting liquid 10; a sample unit 12 for dispensing a sample 21 into the device for transporting liquid 10; a reagent unit 13 for dispensing into the device for transporting liquid 10 a reagent 25 kept in a reagent tub; a detection unit 14 for detecting the sample 21 kept in the sample tub, for example, for measuring the internal ingredient of the sample 21; and a drain unit 15 for draining the sample 21, the reagent 25, and the oil droplet 2. In the sample unit 12 the sample 21 and oil 22 are prepared, which can be introduced into the device for transporting liquid 10 by means of a sample probe 16 and an oil probe 17, respectively, through one region 23, i.e., a sample introducing port.

In the reagent unit 13, the reagent 25 and oil 22 are prepared, which can be introduced into the device for transporting liquid 10 through one region 24, i.e., a reagent introducing port, by means of a reagent probe 18 and an oil probe 17, respectively.

The detection unit 14 is installed adjacent to the measurement section, which is installed in at least a part of a liquid-transporting passage which joints the introducing section for samples, etc. and the drain section.

In the drain unit 15, a sipper 19 and a waste liquid tank 27 are arranged, and the liquid detected in the detection unit is drained by the sipper 19 from an outlet 26 to the waste liquid tank 27. At the beginning, in the sample unit 12, a certain amount of oil 22 kept in the oil tub is supplied from the oil probe 17 into the sample introducing port 23, and thereafter, a certain amount of the sample 21 is sucked into the sample probe 16, and a certain amount of the sucked sample 21 is discharged into the device for transporting liquid 10 from the sample introducing port 23, thereby dispensing the sample 21. Accordingly, a certain amount of oil dispensed and a certain amount of sample dispensed are placed in the device for transporting liquid 10, correspondingly. Moreover, at this time, by introducing the sample after supplying the oil into the sample introducing port 23, the sample can be introduced without adhering to the surface of the device for transporting liquid. On the other hand, in the same manner, in the reagent unit 13, after supplying a certain amount of oil 22 from the oil probe 17 into the reagent introducing port 24, a certain amount of reagent 25 is discharged from a reagent dispenser 18 to dispense the reagent 25. Accordingly, a certain amount of oil dispensed and a certain amount of reagent dispensed are placed in the device for transporting liquid 10, correspondingly. Moreover, in the same manner as in the sample, by introducing the reagent after supplying the oil into the reagent introducing port 24, the reagent can be introduced without adhering to the surface of the device for transporting liquid. The sample 21 and reagent 25 dispensed into the device for transporting liquid 10 are transported in the device for transporting liquid 10, respectively, detected in the detection unit 14, sucked from the outlet 26 by the sipper 19 of the drain unit 15, and are drained into the waste liquid tank 27.

Figure 17:
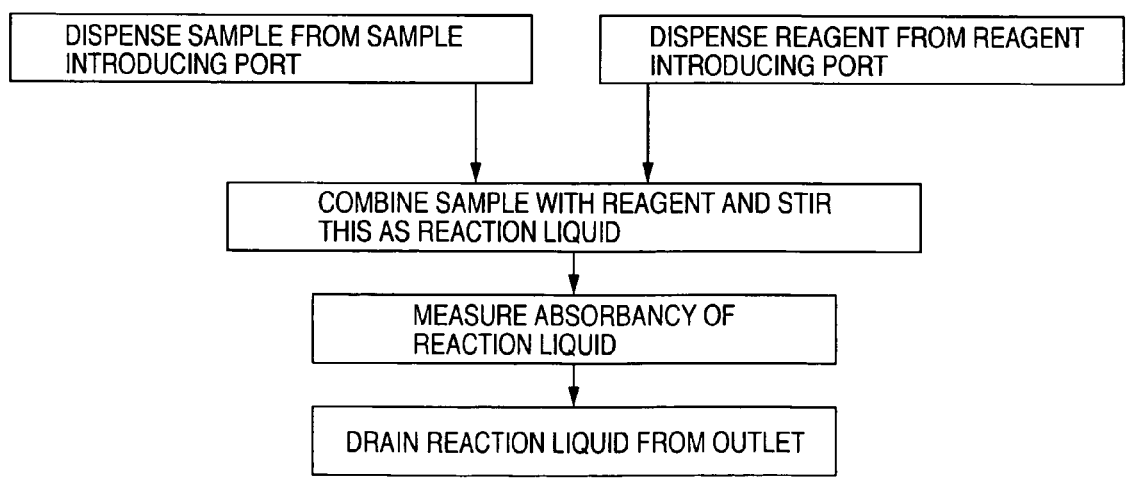
FIG. 17 is a view showing the operation procedure in the device for transporting liquid at the time of applying the invention to a system for analyzing.

FIG. 17 shows an example of a flow of the operation in the device for transporting liquid 10. In the device for transporting liquid 10, first, the sample 21 is dispensed from the sample introducing port 23, and the reagent 25 is dispensed from the reagent introducing port 24, and thereafter, the sample 21 dispensed and the reagent 25 dispensed are mixed to make a reaction liquid 31, and thereafter, the absorbancy of the reaction liquid 31 is measured, and finally the reaction liquid 31 is drained from the outlet.

Figure 18:
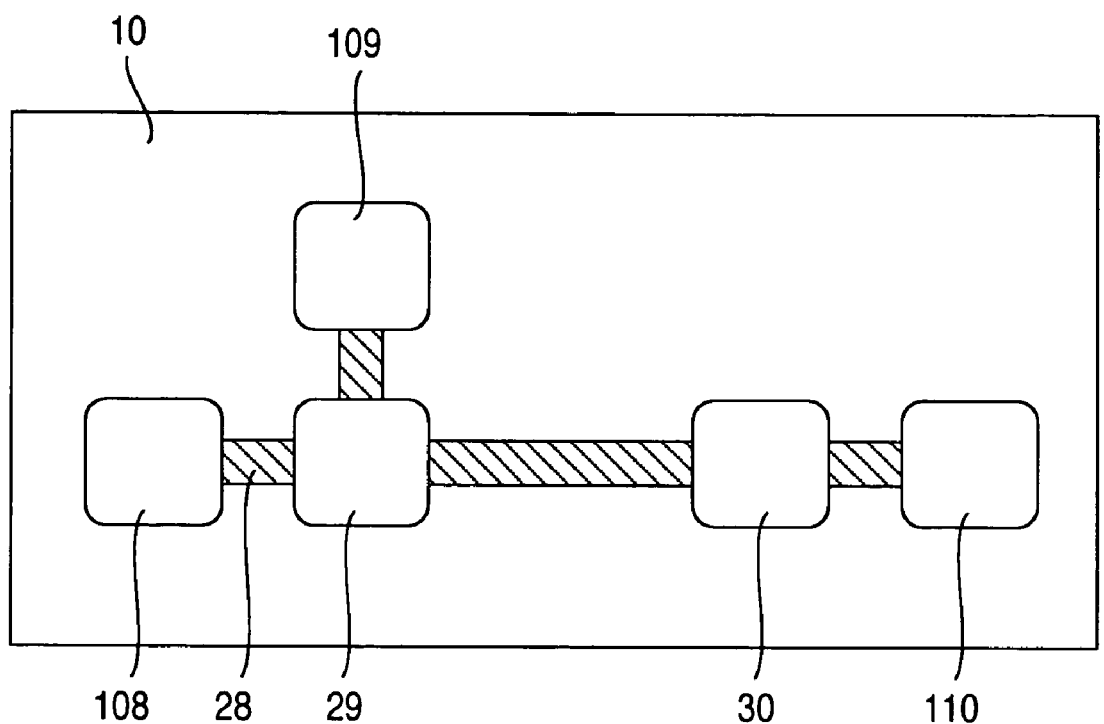
FIG. 18 is a layout view of each part in the device for transporting liquid of the invention.

FIG. 18 shows a layout view of each part for carrying out each operation in the device for transporting liquid 10. In the device for transporting liquid 10, corresponding to each operation of FIG. 17, there exist: a sample introducing section 108 for introducing the sample 21, a reagent introducing section 109 for introducing the reagent 25, a mixing section 29 for combining the sample 21 and reagent 25 to stir as the reaction liquid 31, a measurement section 30 for measuring the reaction liquid 31, and a drain section 101 for draining the reaction liquid 31. Each part is arranged in the device for transporting liquid 10 in the order of the operation flow of FIG. 17, and the connection between the respective parts is made with the liquid-transporting passage 28. Control electrodes are arranged in at least a part of each of the liquid-transporting passage 28, the sample introducing section 108, the reagent introducing section 109, the mixing section 29, the measurement section 30, and the drain section 110, and under control of the applied voltage to the control electrodes, the transporting and analysis of the liquids of a sample, reagent, or the like are controlled. The measurement section 30 is installed in at least a part of the liquid-transporting passage. The sample 21 dispensed from the sample introducing section 108 is transported through the liquid-transporting passage 28, and is then mixed, in the mixing section 29, with the reagent 25 similarly dispensed from the reagent introducing section 109 to make the reaction liquid 31, which is then transported through the liquid-transporting passage 28, and the ingredient thereof is measured in the measurement section 30, and thereafter the reaction liquid 31 is transported and drained at the drain section 110. In this way, by arranging from the introducing section of the liquid through the drain section in accordance with the sequence of each operation in the device for transporting liquid, a plurality of operations can be easily carried out to a plurality of samples.

Figure 19:
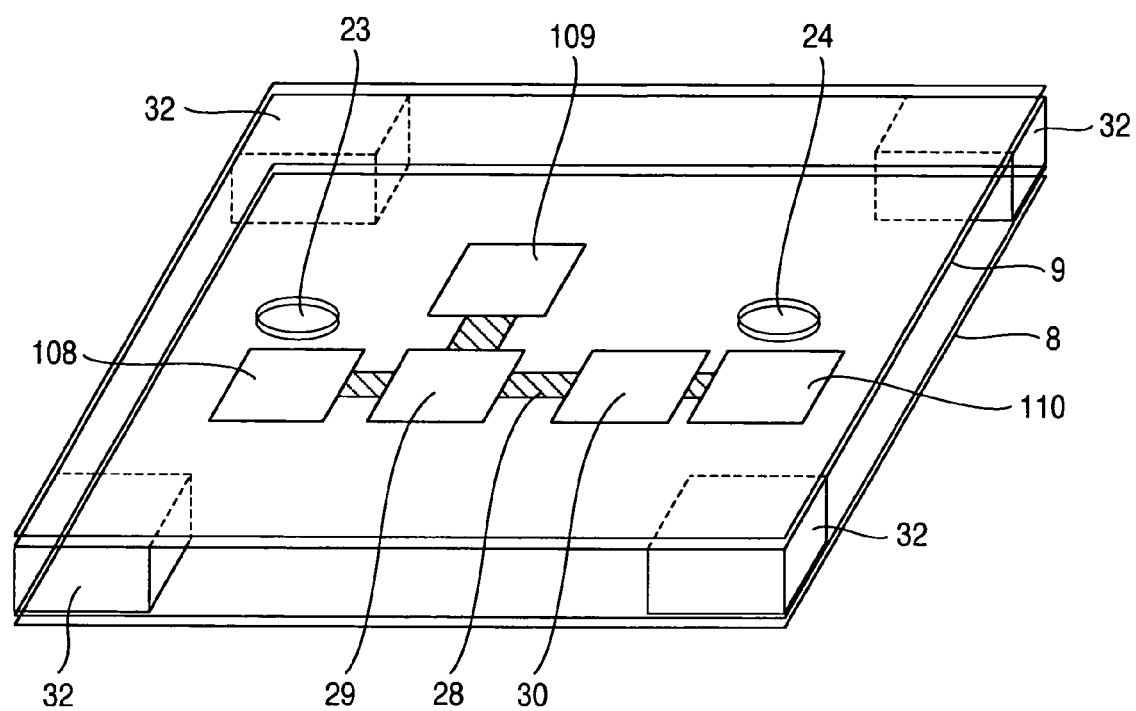
FIG. 19 is an outline view of the device for transporting liquid of the invention.

FIG. 19 shows an outline view of the device for transporting liquid used in this example. In this example, spacers 32 with a height of 0.5 mm are sandwiched between two upper and lower substrates 8 and 9 to fix so as to keep a certain space. In case of the device for transporting liquid whose inside is filled with oil, the side face needs to be sealed so that oil may not leak therethrough, however, because in this example, the liquid is enclosed by an oil droplet, the oil droplet being fractionated by air, and is then transported, the side face does not need to be treated such that oil may not leak therethrough, and the mounting of the device for transporting liquid will be simplified.

Figure 20:
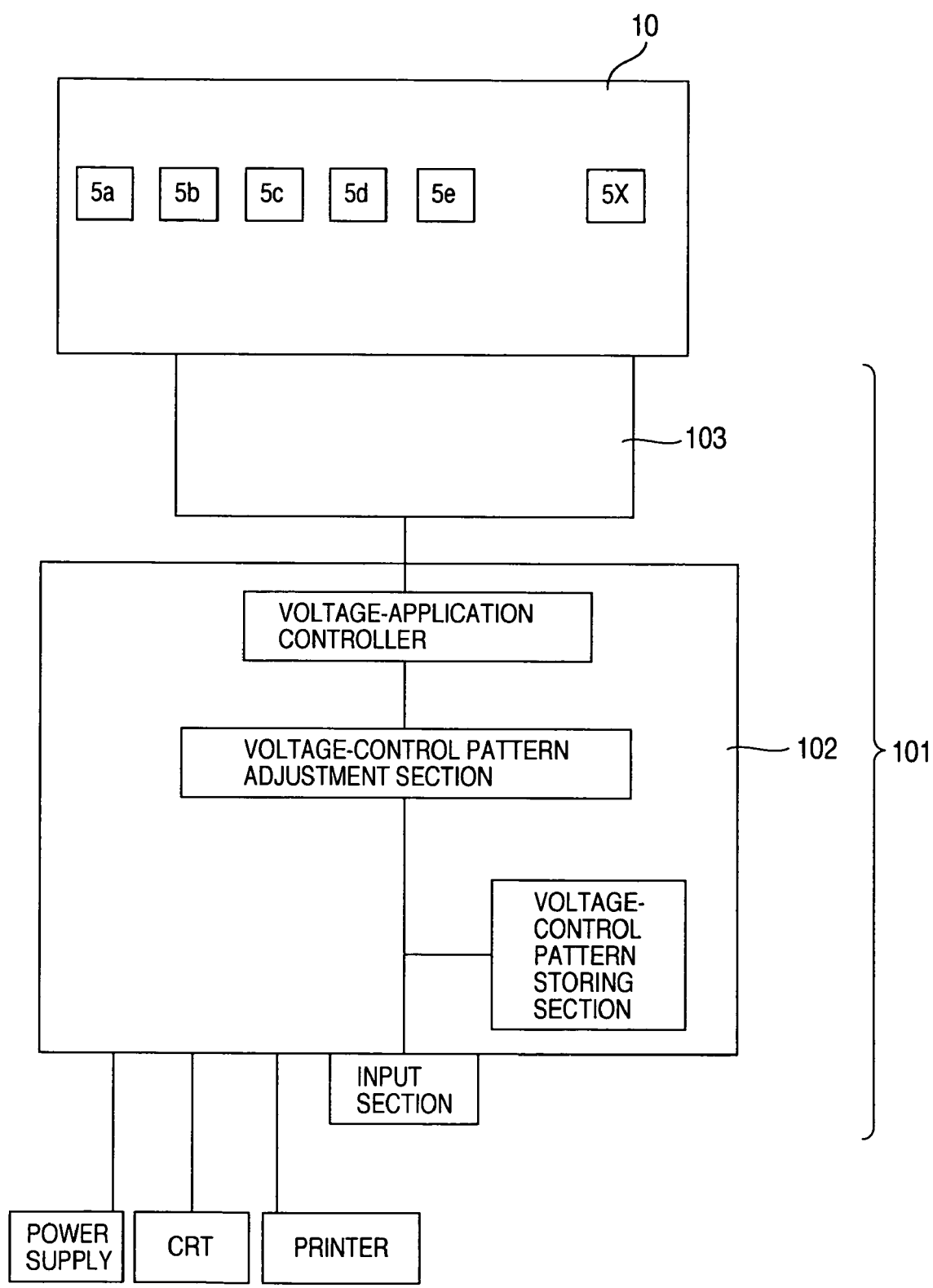
FIG. 20 is a schematic view of a control system of the invention.

FIG. 20 shows a configuration of a voltage controller 101 for manipulating the liquid 1 in the device for transporting liquid 10. This controller is provided in the system for analyzing shown in FIG. 16, and it includes a computer for controlling 102, and an interface 103 for applying an application voltage controlled by the computer for controlling 102 to a predetermined electrode of the device for transporting liquid 10. A CRT, a printer, and a power supply are coupled to the computer for controlling. The computer for controlling comprises: an input section for inputting the conditions concerning a target for analysis and the method for transporting liquid suitably; a voltage-control pattern storing section for storing a voltage-control pattern corresponding to the various methods for transporting liquid; a voltage-control pattern adjustment section for defining a combination of the voltage-control pattern corresponding to a target for analysis based on the information inputted from the input section; and a voltage-application control section for applying voltages, to the device for transporting liquid 10, corresponding to the combination of the voltage-control pattern defined in the voltage-control pattern adjustment section. The interface 103 is connected to the control electrode 5, and when controlling the liquid 1, a voltage under control of the voltage-application control section is applied to a predetermined electrode through the interface 103 according to the information inputted from the input section.

Figure 21:
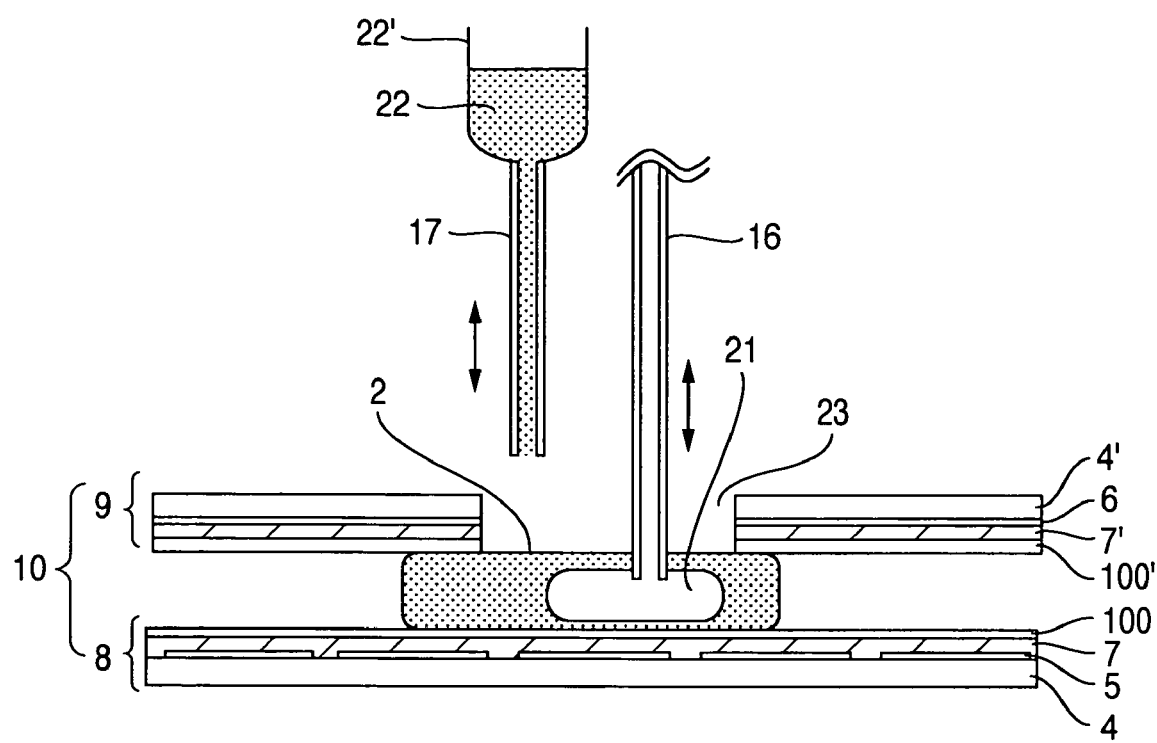
FIG. 21 is a cross sectional view of a sample introducing port in the embodiment 5 of the invention.

FIG. 21 shows an example of the sectional configuration of the sample introducing section 108. The oil probe 17 for introducing the oil 22, which is kept in the container, into the sample introducing port 23 of the upper substrate 9, and the sample probe 16 for dispensing the sample 21 kept in the container, are installed vertically and movably, respectively. In addition, also as for the reagent introducing section 109, the same configuration as FIG. 21 can be employed except for substituting the sample probe 16 with the reagent probe 18 for dispensing the reagent 25, which kept in the container. The sample probe 16, while being in contact with the oil droplet 2 which is fractionated and dispensed into the sample introducing section 108, fractionates the sample and dispense it into the oil droplet 2. Accordingly, the sample can be placed within the oil droplet, for certain. In addition, lipophilicity may be given to at least a part of the outside of the sample probe 16 by applying a water-repellent film or the like. In this case, the affinity between the oil 22 and the sample probe 16 can be improved, and the sample 21 can be discharged into the oil droplet 2 more certainly.

Moreover, although, here, there has been shown a configuration wherein one sample 21 is discharged as one droplet in one oil droplet 2, it is also possible to move the one droplet by applying a voltage to the control electrode 5 after discharging one droplet, and further discharge one or more samples 21 into the oil droplet 2. Also in this case, the dispensing liquid can be carried out without affecting the liquids other than the oil droplet 2, the oil droplet 2 being the target for discharge, the liquids being placed in the device for transporting liquid. In this manner, the above formation is also possible in the case where a plurality of liquids exist within one oil droplet as shown in FIG. 8.

Figure 22A:
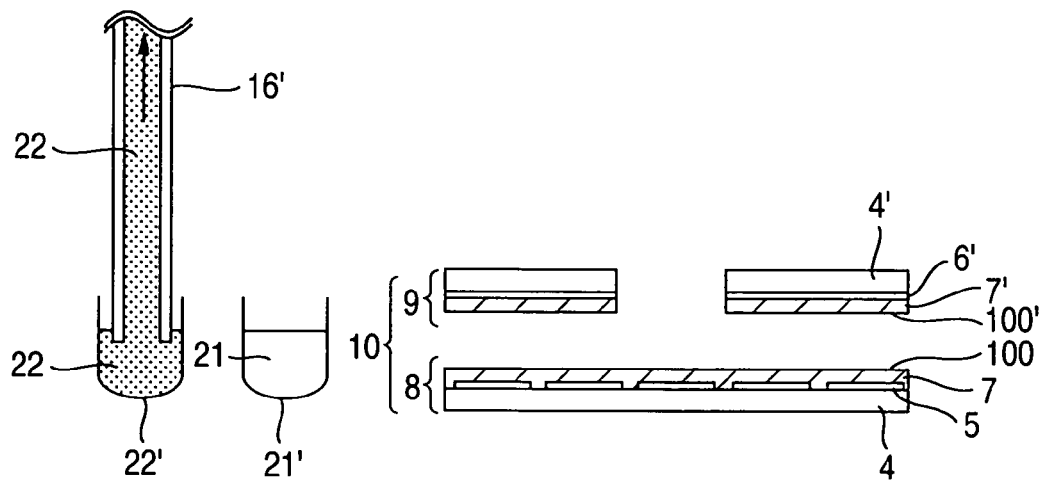
FIG. 22A is a cross sectional view of a sample introducing port in the embodiment 5 of the invention.
Figure 22B:
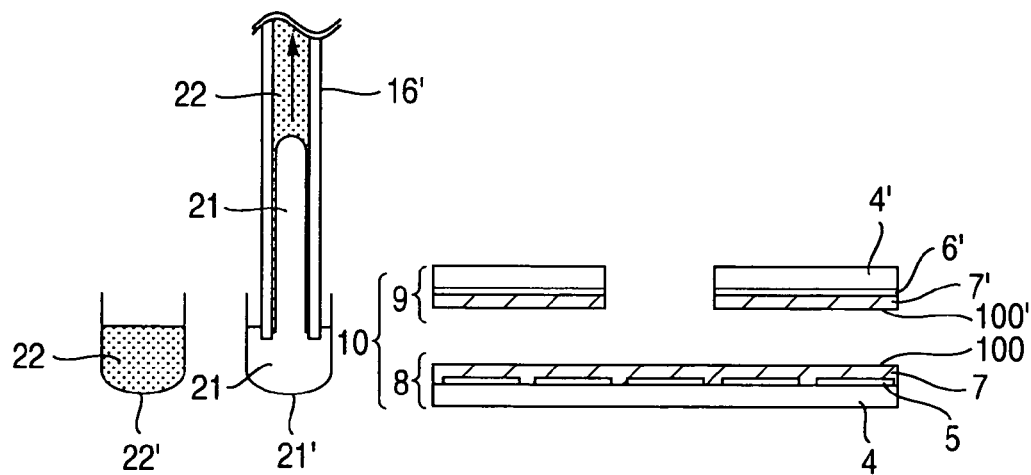
FIG. 22B is a cross sectional view of the sample introducing port in the embodiment 5 of the invention.
Figure 22C:
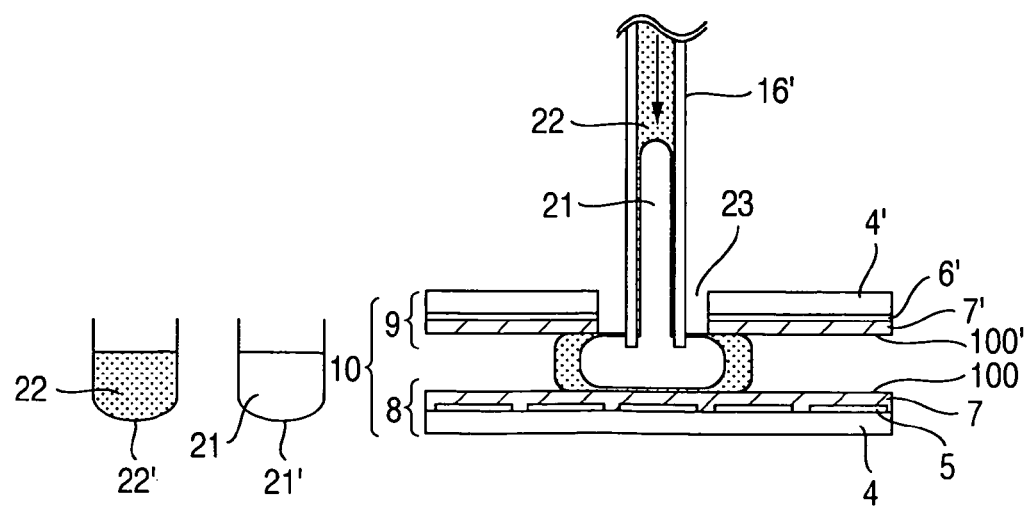
FIG. 22C is a cross sectional view of the sample introducing port in the embodiment 5 of the invention.

Moreover, a configuration may be employed, wherein, as shown in FIG. 22, a container 22' for storing oil 22 and a container 21' for storing a sample are prepared, and, first, as shown in FIG. 22A, the oil 22 is sucked from the container 22' with a probe 16', and thereafter, by sucking the sample 21 from the container 21', as shown in FIG. 22B, the sample 21 is enclosed with the oil 22, which is stored inside the probe 16' due to the sucking, and then the sample 21 together with the whole oil 22 is discharged into the device for transporting liquid 10 to disperse, as shown in FIG. 22C. In this manner, it is not necessary to install two types of probes, i.e., the sample probe and oil probe, as the mechanism for dispensing into the device for transporting liquid, and thus the mechanism can be simplified. In the configuration of the present invention, because the sample 21 is discharged in the oil droplet 2, the probe will not receive a force from the surface tension of the gas-liquid interface when passing through the gas-liquid interface between the oil droplet 2 and the air 3, and thus the sample 21 will not adhere to the probe 16', and consequently, even a minimal amount of sample 21 can be desorbed and dispensed stably. Moreover, also in the reagent introducing section 109, the reagent 25 can be dispensed in a similar manner. Conventionally, in the device for transporting liquid 10 whose inside is filled with oil 22, the rise and fall in the oil interface and an oil flow due to the introduced liquid occur when carrying out such dispensing, however, like in this example, by enclosing the periphery of the liquid with a fractionated oil droplet it is possible to dispense without affecting other liquids in the device for transporting liquid.

Figure 23:
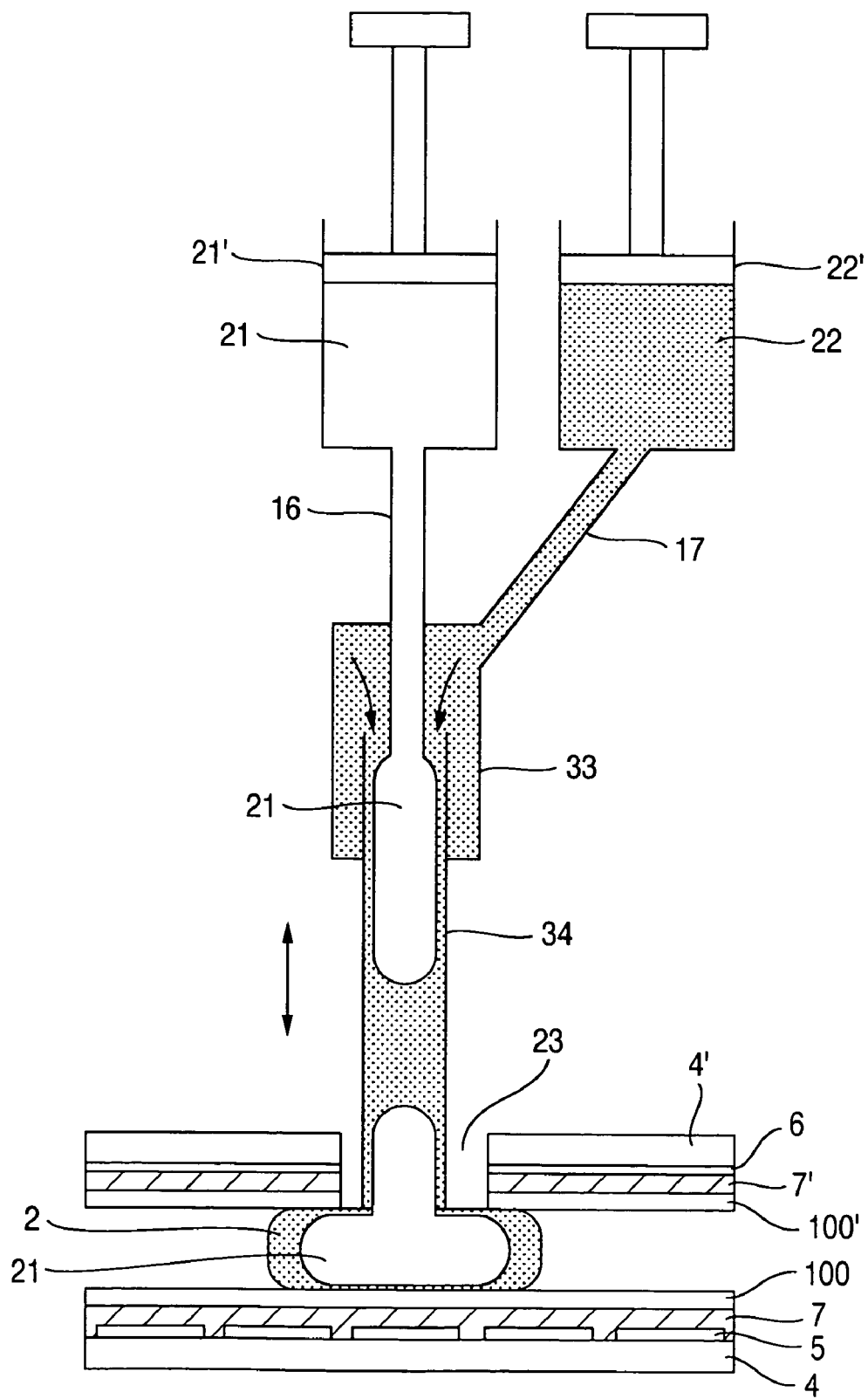
FIG. 23 is a cross sectional view of the sample introducing port in the embodiment 5 of the invention.

Moreover, although in this example, the oil probe 17 is used for supplying the oil 22 at the sample introducing section 108, it is also possible to dispense the sample 21 enclosed with oil 22 into the device for transporting liquid 10 using a flow cell. FIG. 23 shows a sectional configuration of the reagent introducing section in the case where a flow cell is used. In addition, also in the reagent introducing section 109, the reagent 25 can be dispensed in a similar manner. The sample probe 16 and oil probe 17 are coupled to a flow cell 33, from which a flow-cell probe 34 extends to the device for transporting liquid 10. After discharging a certain amount of sample 21 into the flow cell first, a certain amount of sample 21 is separated by passing the oil 22 around the sample probe 16 and pushing out the sample together with the whole oil 22 into the device for transporting liquid 10, the sample 21 enclosed by the oil droplet 2 is dispensed. By making such a configuration, the liquid can be dispensed into the device for transporting liquid while the sample is kept in contact with the oil.

Figure 29A:
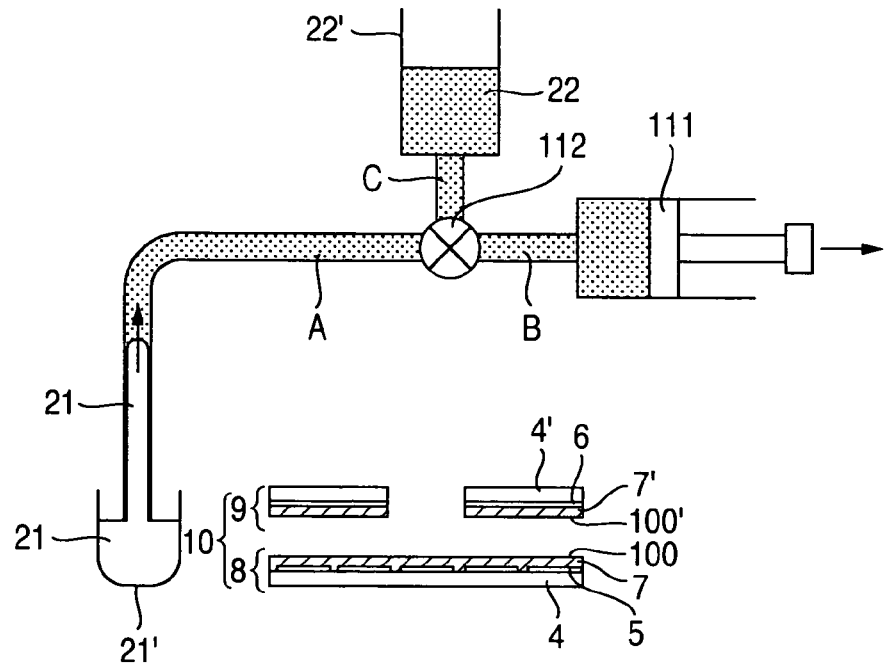
FIG. 29A is a schematic view explaining the embodiment 5 of the invention.
Figure 29B:
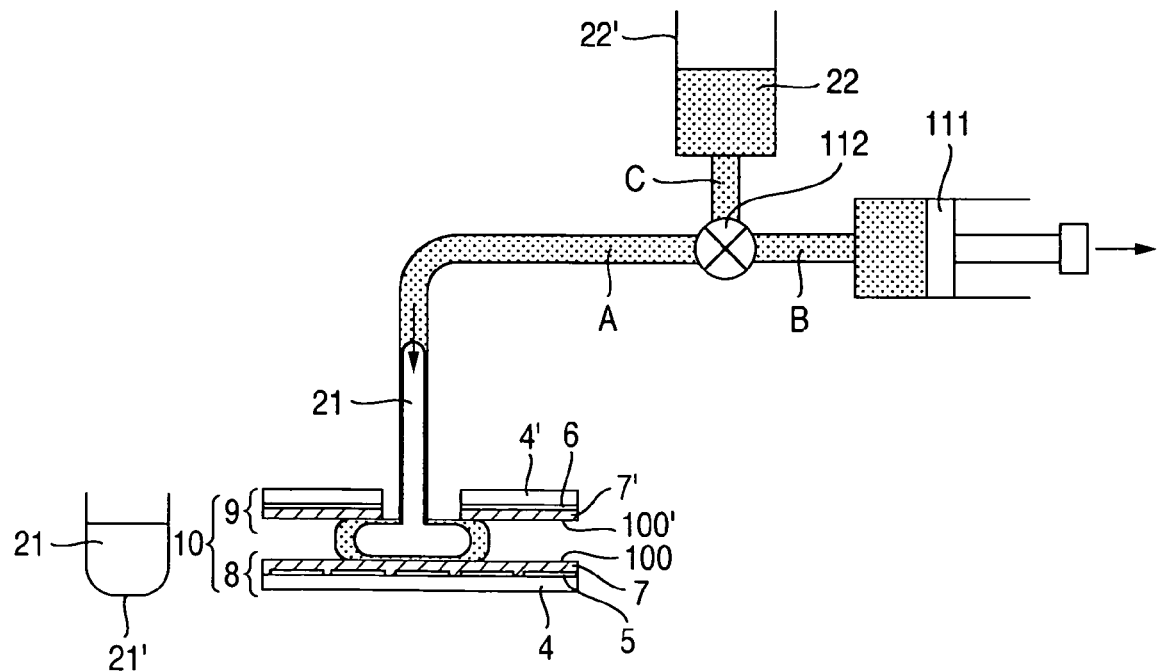
FIG. 29B is a schematic view explaining the embodiment 5 of the invention.

Moreover, as shown in FIG. 29, the oil 22 may be supplied using a bulb 112. In this case, the time to suck oil can be reduced, which leads to the reduction in time to supply oil in dispensing a sample sequentially, and the throughput can be increased. At the time of supplying oil, the B and C sides of the bulb are jointed to store oil into a syringe using a syringe 111. Then, as shown in FIG. 29A, the A and B sides of the bulb are jointed to suck the sample 21 with the syringe 111. Then, as shown in FIG. 29B, the sample 21 can be introduced into the device for transporting liquid 10 using the syringe 111, and thereby the sample 21 can be dispensed. That is, a liquid supplying section having the bulb and the syringe sucks the sample after sucking the oil, and then it discharges the sample enclosed by the oil and introduces the same as a sample enclosed by the oil droplet. In addition, also in the reagent introducing section 109, the reagent 25 can be dispensed in a similar manner.

In the mixing section 29, the combining and stirring of the sample 21 and reagent 25 are carried out by the method shown in the example 2. According to this configuration, a plurality of liquids can be manipulated in the device for transporting liquid stably and independently without transmitting an oil flow generated by the mixing of a plurality of liquids to other liquids except the liquid currently being mixed.

Figure 24:
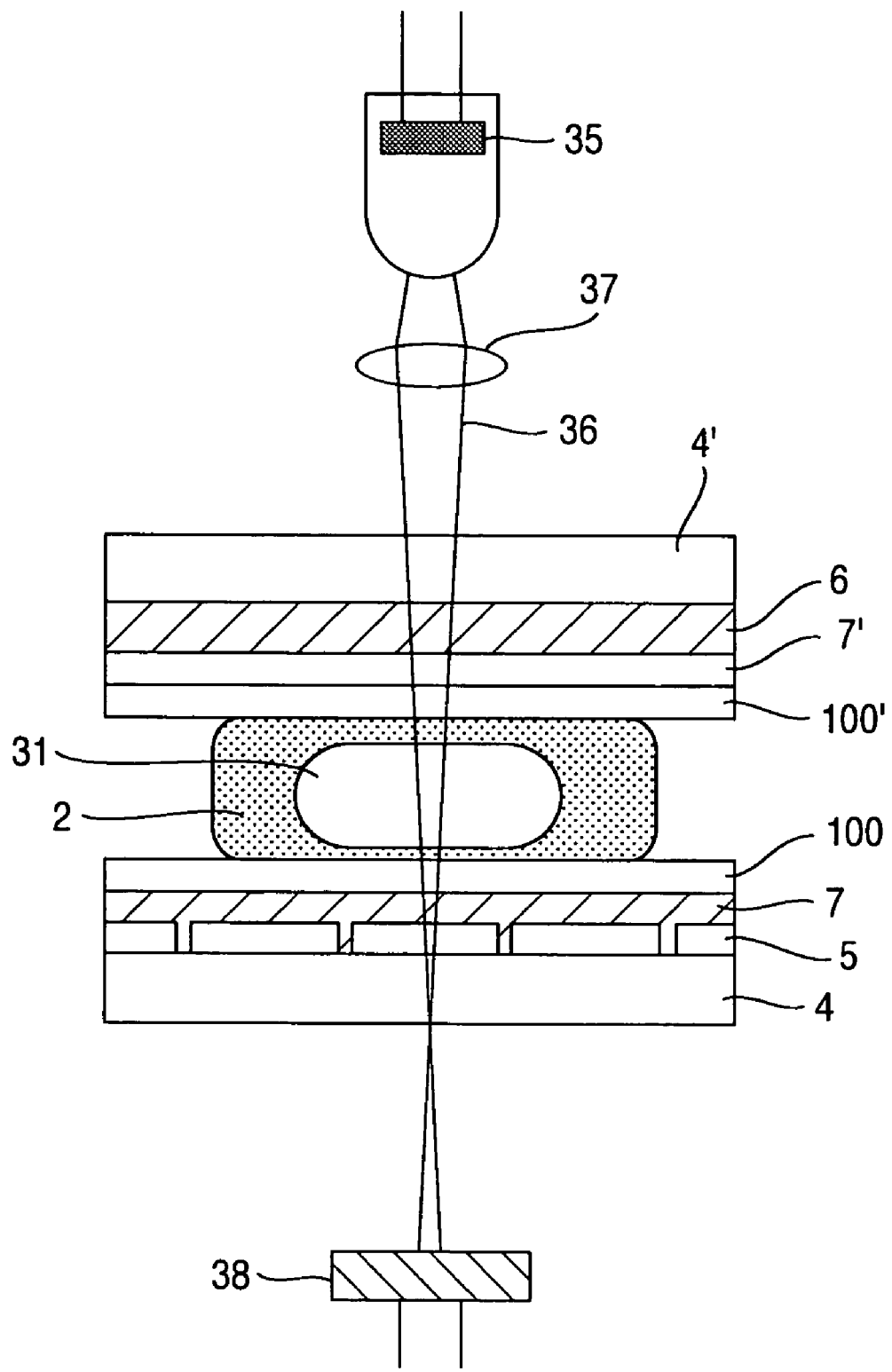
FIG. 24 is a cross sectional view of a measurement section in the embodiment 5 of the invention.
Figure 25:
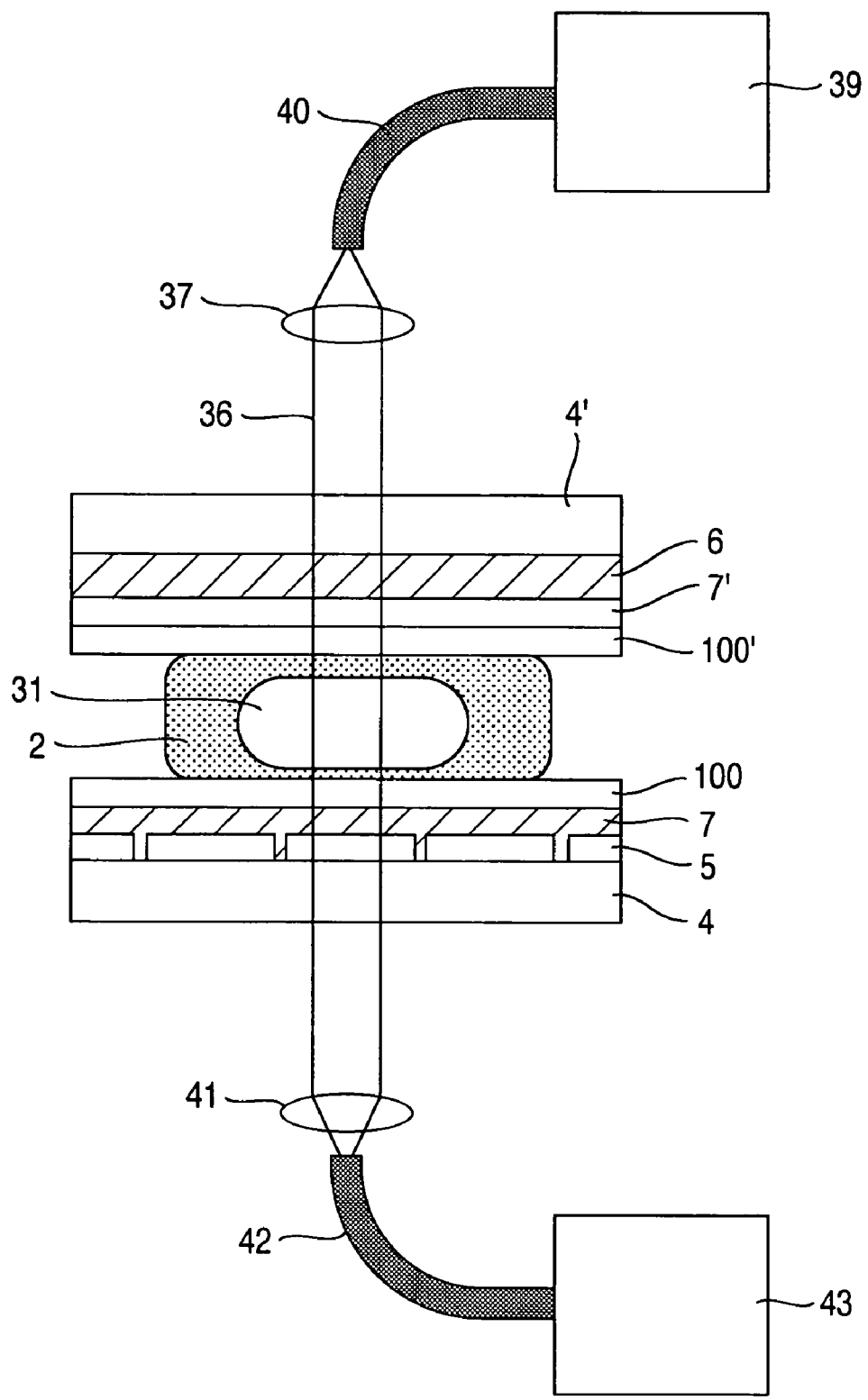
FIG. 25 is a cross sectional view of a measurement section in the embodiment 5 of the invention.

FIG. 24 shows a configuration of the detection unit 14 and the measurement section 30. In this example, the absorbancy is measured using LED 35. Light 36 from LED 35 is incident upon a reaction liquid 31 through an irradiation lens 37, and the transmitted light is detected by a photo diode 38. Although in this example LED 35 is used, a halogen lamp 39 may be used as shown in FIG. 25. The light 36 introduced through an irradiation optical fiber 40 is irradiated at the irradiation lens 37 in the measurement section 30, the transmitted light is condensed into a condensing optical fiber 42 through a condenser lens 41, and the light is dispersed into required wavelengths at a detection system 43 provided with a dispersing means, for detection. Moreover, although in this example, the measurement is carried out with light in the measurement section, the impedance of a liquid or an oil droplet may be measured using electrodes, and the ingredient inside the liquid may be measured electrically by arranging the electrodes provided with an ion induced membrane.

In the case where the inside of the device for transporting liquid is filled with oil, it can be assumed that if air bubbles come in from the introducing port or the outlet, the air bubbles come in contact with the liquid to affect the transporting and measurements of the liquid, and therefore, it is assumed that in order to remove the air bubbles from the inside of the oil, the air bubbles are contacted to the interface between the oil and the air, and the whole oil are removed from the device for transporting liquid, and then, the oil is introduced once again, thereby removing the air bubbles. By enclosing the liquid with an oil droplet like in this example, the air bubbles can be easily contacted to the interface between the oil and air, and the air bubbles can be removed from the inside of the oil droplet. This also allows for the measurement to be carried out stably.

Figure 26:
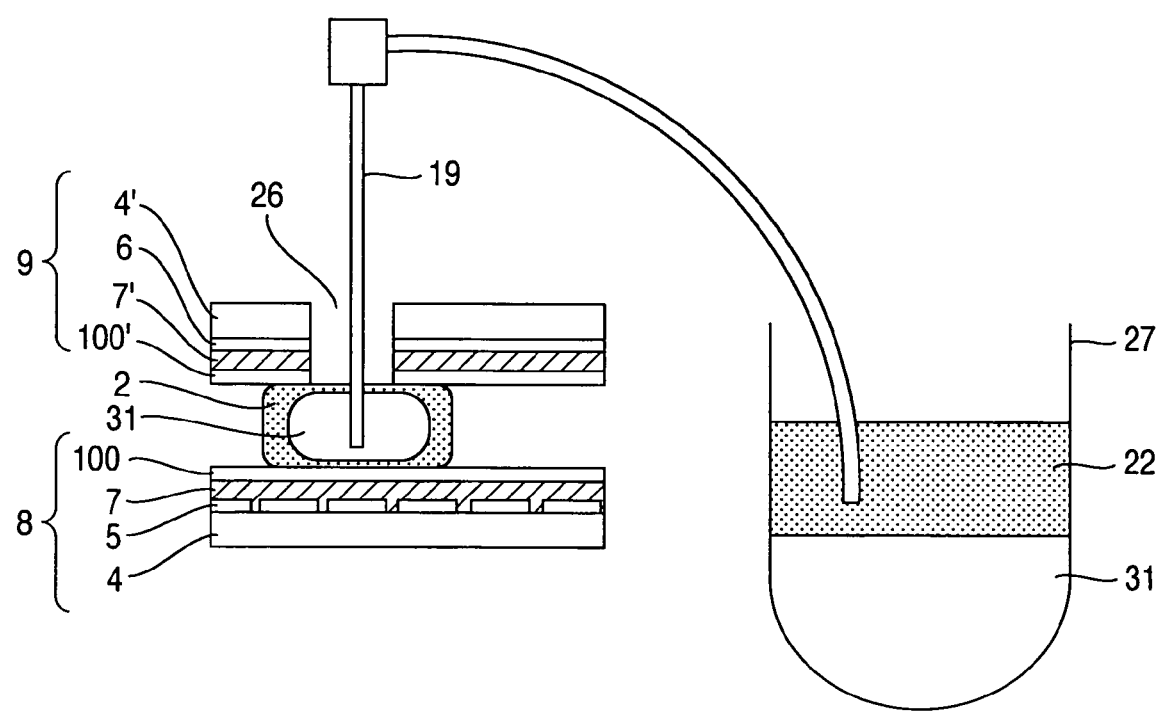
FIG. 26 is a cross sectional view of an outlet in the embodiment 5 of the invention.

FIG. 26 shows a sectional configuration of the drain section 110. The reaction liquid 31 and the oil droplet 2 transported to the outlet 26 are sucked by the sipper 19 of the drain unit 15, and are drained into the waste liquid tank 27. In the case where the inside of the device for transporting liquid is filled with oil, a flow occurs in the oil by sucking the liquid and oil when draining the liquid, however, as in this example, by draining the liquid enclosed by the oil droplet, a plurality of liquids can be manipulated stably without having influence on other liquids in the device for transporting liquid, the influence being caused by an oil flow. Moreover, because in the waste liquid tank 27, the oil droplet 2 is drained and the gathered oil 22 and reaction liquid 31 will separate due to the differences in their specific gravities, the oil or reaction liquid will be treated easily even when a number of reaction liquids and oil droplets enclosing the same are drained. Moreover, in the conventional device for transporting liquid which is filled with oil, the oil which touched upon the sample and reagent will touch upon samples and reagents which are to be mobilized next, and consequently the ingredient of the sample and the reagent will mix to each other through the oil. On the other hand, according to this configuration, because the sample, the reagent or the reaction liquid, as well as the oil which touched upon the same can be drained together, the ingredient will not mix with the next sample and reagent, and thus the oil in the device for transporting, liquid can be kept clean.

Figure 27:
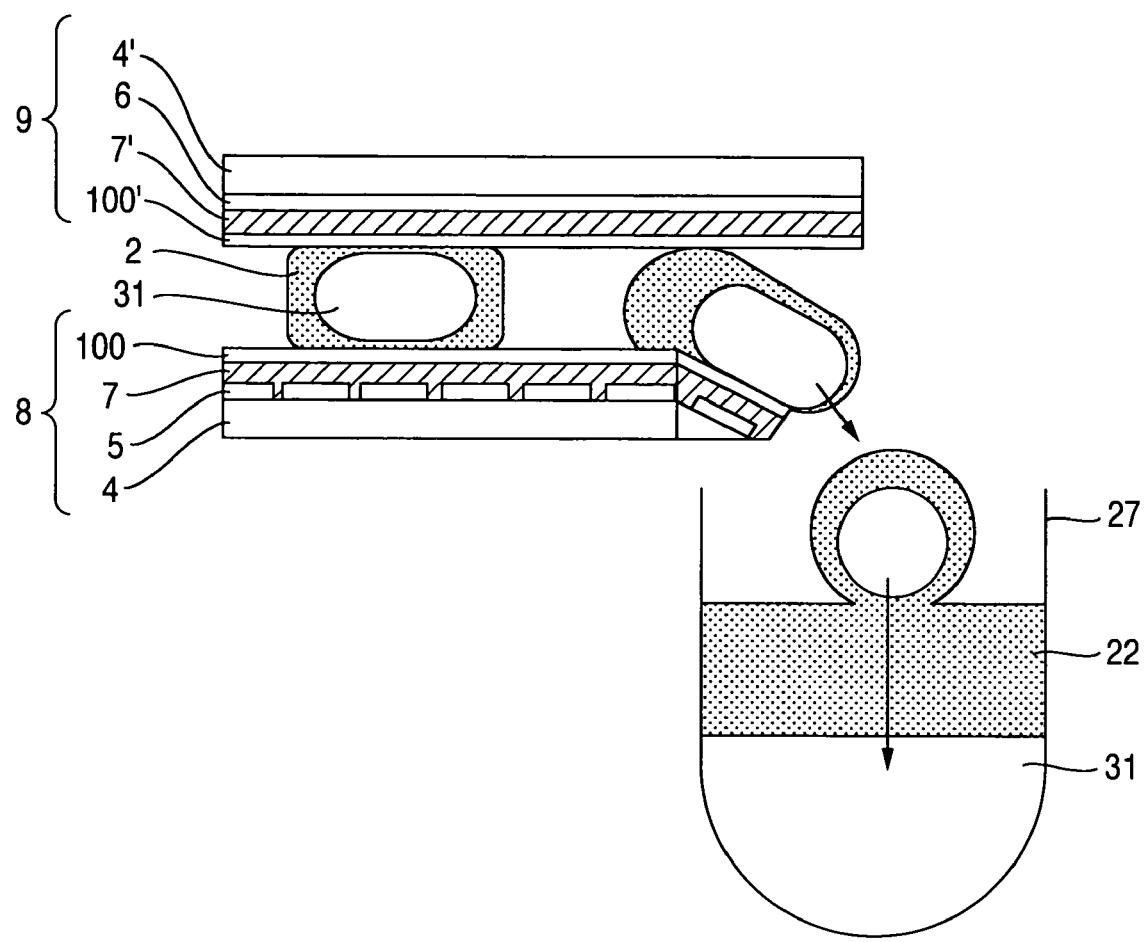
FIG. 27 is a cross sectional view of the outlet in the embodiment 5 of the invention.

The draining may be carried out from the side face or bottom face of the device even when the outlet and sipper 19 are not arranged. FIG. 27 shows an example. A slope is provided in the lower substrate 8, liquid is transported to the outlet having a gradient, and then the liquid will be drained to a waste liquid tank arranged thereunder, with the help of gravity. In this case, by connecting the waste liquid tank to the earth, an electric field may force the liquid to be drained to the waste liquid tank side. In the case where the inside of the conventional device for transporting liquid is filled with oil, the side face thereof is sealed such that the oil may not leak therethrough, and it is therefore assumed that it is difficult to drain the liquid 1, however, according to this configuration, it is not necessary to form the side face or bottom face such that the oil may not leak therethrough, and the liquid can be drained from the side face or the bottom face, and thus the configuration of the drain section will be simplified.

According to the configuration of this example, by enclosing a sample and a reagent with an oil droplet and transporting them, respectively, manipulations can be carried out stably to multiple liquids in the device for transporting liquid. Moreover, although in the above examples an application to an system for analyzing has been targeted for, the present invention can be, of course, also applied to a reaction system wherein a reaction liquid and an oil drained out of the outlet are separately gathered into separate containers, respectively, and thereby a plurality of liquids are reacted and formed in the device for transporting liquid, and is applied to a mixing system for forming a composition of a plurality of liquids.

Embodiment 6

Figure 28:
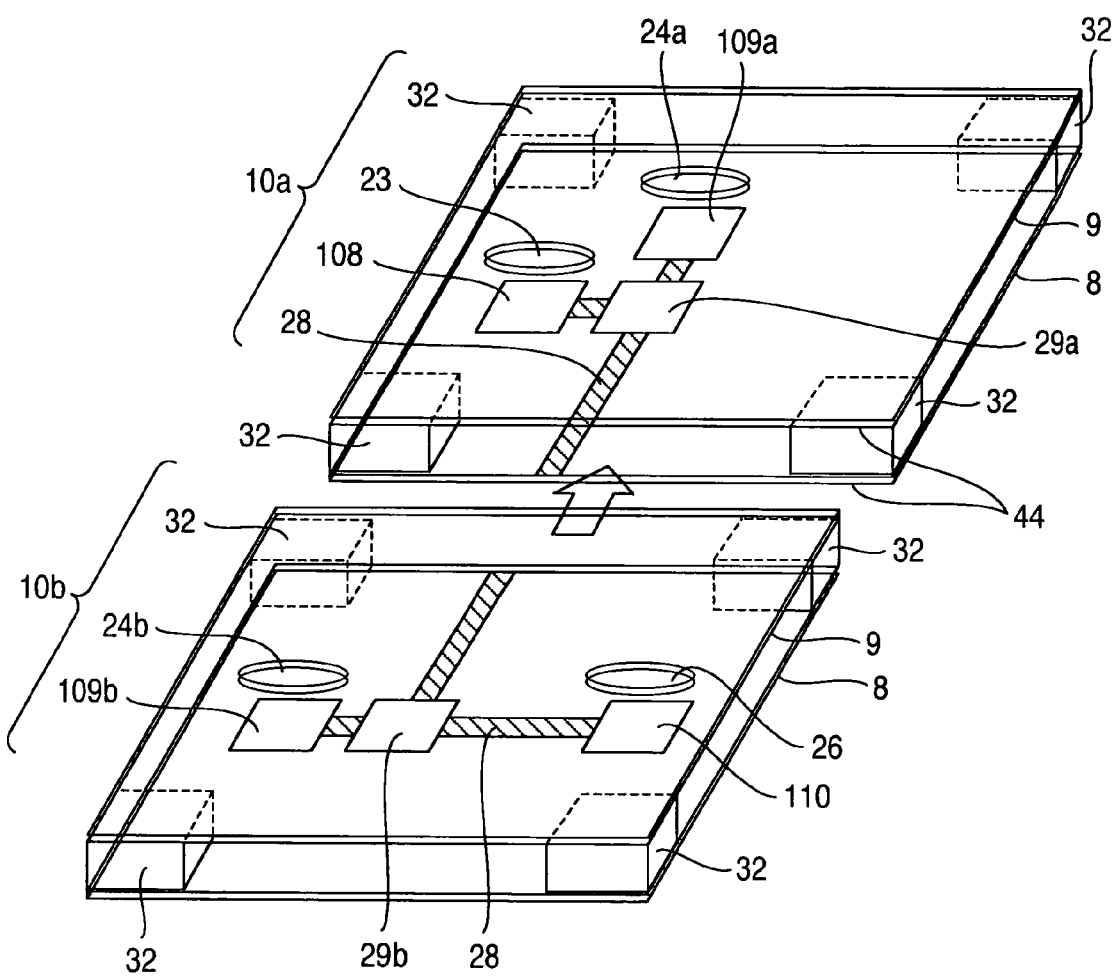
FIG. 28 is a schematic view explaining an embodiment 6 of the invention.

In this example, a means for jointing a plurality of devices for transporting liquid is described. By using a device for transporting liquid whose side face is not sealed, a plurality of devices for transporting liquid are combined for use as one device for transporting liquid. FIG. 28 shows an example in which two device for transporting liquids are combined. The side face of the device for transporting liquid is open to the outside, and a plurality of devices for transporting liquid 10a and 10b are connected using a bonding agent 44 to the side face of the device for transporting liquid. Although for the bonding agent 44, a silicone system adhesive was used, a Teflon (registered trademark) system water-repellent film or the like may be used to contact the devices for transporting liquid to each other. Because in case of a Teflon (registered trademark) system water-repellent film, it is not necessary to bond, the device for transporting liquids can be easily separated again after the connection. Moreover, the liquid-transporting passages in the respective devices for transporting liquid are arranged so as to function as one liquid-transporting passage when the devices are connected. A sample is introduced from the sample introducing port 23 into the device for transporting liquid 10a, and mixed with a reagent introduced from the reagent introducing port 24a in a mixing section 29a, then transported through the liquid-transporting passage 28, and moved to the device for transporting liquid 10b. The sample is then mixed, in a mixing section 29b, with the reagent introduced from a reagent introducing port 24b in the device for transporting liquid 10b, and is drained from the outlet 26. In this way, because liquids can be transported across a plurality of devices for transporting liquid, the reacting with multiple reagents can be carried out, and a plurality of each part for manipulation can be arranged by connecting the devices for transporting liquid when carrying out multiple manipulations. Moreover, in the case where multiple liquids are manipulated independently, one device for transporting liquid may have a plurality of liquid-transporting passages therein, however, multiple liquids may be distributed to a plurality of devices for transporting liquid using the devices for transporting liquid, and thereby the manipulations may be carried out in the respective devices for transporting liquid. It was difficult to connect the devices for transporting liquid because conventionally the inside of the device for transporting liquid which is filled with oil has the side face sealed, however, according to the present invention, because the side face does not need to be sled such that the oil may not leak therethrough, a plurality of devices for transporting liquid can be connected easily. If a plurality of devices for transporting liquid can be connected like in this example, the device for transporting liquid can be applied to a system for analyzing, a system for reaction, and a mixed system, in which multiple manipulations are carried out to multiple liquids independently.

Embodiment 7

Figure 30:
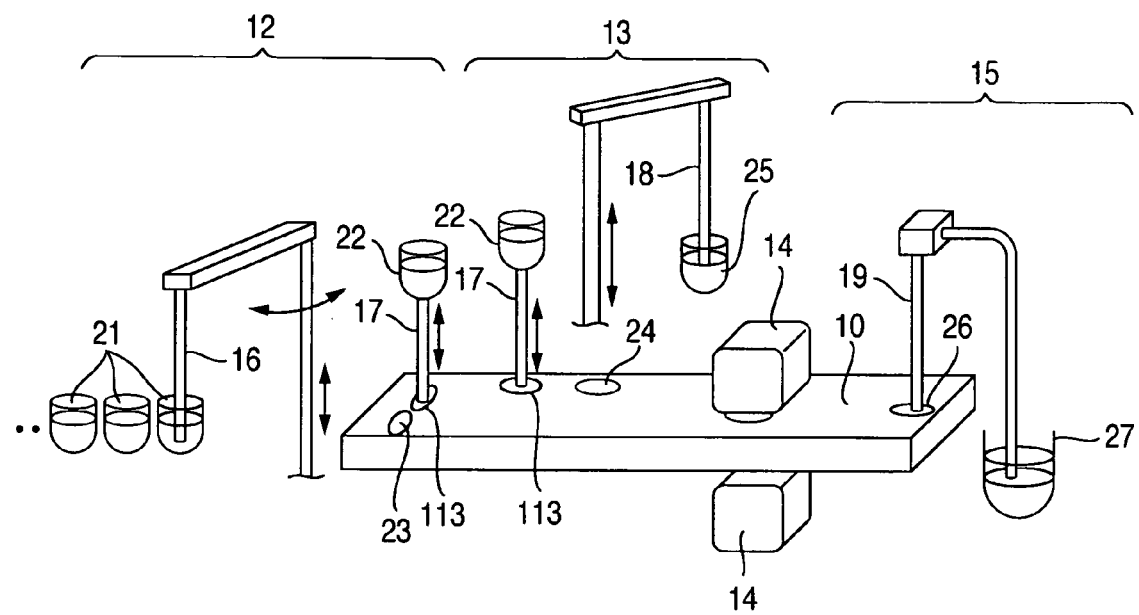
FIG. 30 is a schematic view explaining an embodiment 7 of the invention.

FIG. 30 shows an system for analyzing wherein an oil introducing port 113 is independently provided at the sample introducing port 23 and at the reagent introducing port 24, respectively, and they are introduced into the device for transporting liquid 10 from the separate ports, and the sample 21 liquid is transported and contacted to the oil in the device for transporting liquid 10. With this configuration, liquids enclosed by an oil droplet are easily produced.

Figure 31:
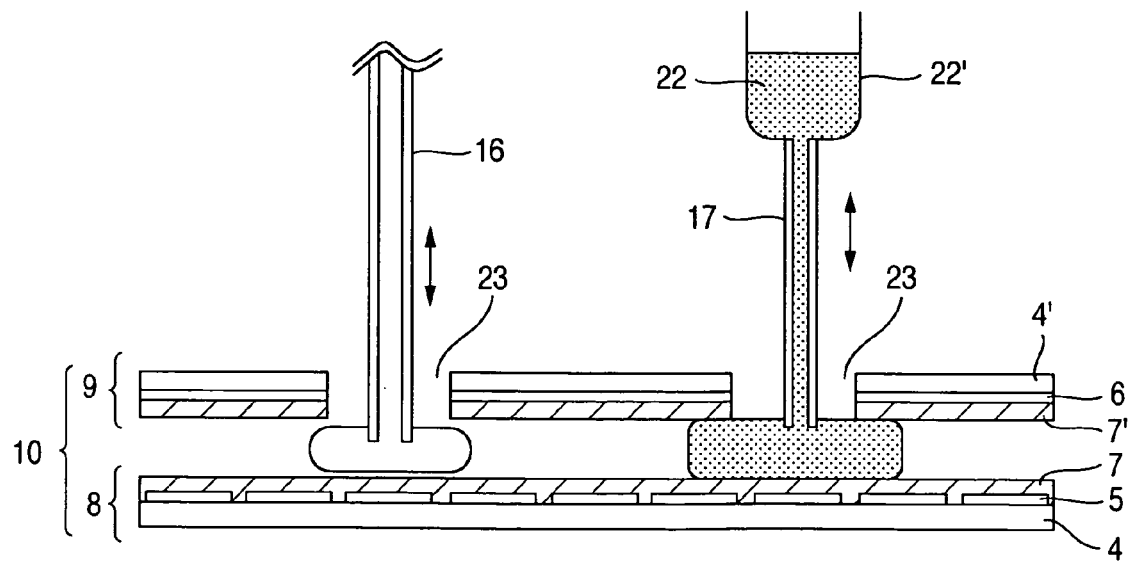
FIG. 31 is a schematic view explaining the embodiment 7 of the present invention.

FIG. 31 shows a sectional view of the sample introducing section. The sample 21 is sucked using the sample probe 16, and is dispensed from the sample introducing port 23. The oil 22 is dispensed from the oil introducing port 113 using the oil probe 17. The sample 21 and the oil 22 introduced respectively are located on the electrodes in which the electrodes are arranged in the device for transporting liquid 10. With the sample 21 and oil 22 resting on the electrodes, at least either one of a sample droplet and an oil droplet can be transported to form a liquid (droplet) enclosed by the oil droplet by means of the procedure shown in the example 4, i.e., the procedures shown in FIG. 14 and FIG. 15. For example, the fractionated and dispensed sample 21 can be transported from the sample introducing section to the oil introducing section along the liquid-transporting passage in which the control electrodes are arranged, so as to be contained by at least a part of the oil 22, which has been fractionated and dispensed into the oil introducing section, and it can be transported as a liquid, which is enclosed and contained by the oil droplet, along the liquid-transporting passage. The configuration of the mixing section and drain section can be made the same as those in the example 6.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A system for analyzing, comprising:
a first unit comprising a means for supplying a first liquid, and a means for supplying a second liquid;
a second unit comprising an introducing section into which the first liquid is introduced from the means for supplying the first liquid, a drain section for draining the first liquid, a liquid-transporting passage which is provided with a plurality of electrodes and which joins the introducing section to the drain section and which is filled with a gas, a measurement section provided in at least a part of the liquid-transporting passage, and a voltage application means for applying a voltage to at least a part of the plurality of electrodes;
a third unit comprising a detection system for detecting the measurement section; and
a fourth unit for draining liquid from the drain section, wherein
the second liquid is immiscible with the first liquid, and the first unit fractionates the first liquid such that the second liquid contains a fractionated first liquid, and supplies it to the second unit,
in the second unit the second liquid containing the fractured first liquid is present in the liquid-transporting passage and fractionated by gas of a periphery, and
the voltage application means applies a voltage to at least a part of the plurality of electrodes as to move a compound of a fractured first liquid and a second liquid along the liquid-transporting passage.

2. The system for analyzing according to claim 1, further comprising a dispense probe which dispenses the first liquid and the second liquid, wherein
the means for supplying the first liquid has a first container for storing the first liquid,
the means for supplying the second liquid has a second container for storing the second liquid, and
after sucking the second liquid from the second container, the dispense probe sucks the first liquid and introduces the sucked second liquid and first liquid into the second unit.

3. The system for analyzing according to claim 1, further comprising a flow cell, and a flow cell probe to be jointed thereto, wherein
the means for supplying the first liquid has a first container for storing the first liquid and a first probe for sucking and discharging the first liquid,
the means for supplying the second liquid has a second container for storing the second liquid, and a second probe for sucking and discharging the second liquid, and
the flow cell probe, into which the first liquid and the second liquid are introduced from the first probe and the second probe, respectively, introduces the compound into the second unit by means of a liquid flow of the second liquid.

4. The system for analyzing according to claim 1, wherein
the means for supplying the first liquid has a the first container for storing the first liquid,
the means for supplying the second liquid has a second container for storing the second liquid, and
a liquid supplying section for supplying the second liquid, after sucking the second liquid from the second container, sucks the first liquid to form the compound and introduces the compound into the second unit.

5. The system for analyzing according to claim 1, wherein the voltage application means applies the voltage as to move a plurality of the compounds, and wherein the periphery of each of the plurality of compounds is filled with the gas.

6. The system for analyzing according to claim 1, wherein the means for supplying the first liquid has a container for storing the first liquid, and a first probe which sucks and discharges the first liquid, wherein when the first probe is in contact with the second liquid which is introduced into the introducing section, it introduces the first liquid to the inside of the introduced second liquid.

7. The system for analyzing according to claim 6, wherein the means for supplying the second liquid has a second probe which sucks and discharges the second liquid.

8. The system for analyzing according to claim 6, wherein the first probe has a water-repellent film provided in at least a part of the external surface thereof.

9. A system for analyzing, comprising:
a first unit comprising a means for supplying a first liquid, and a means for supplying a second liquid;
a second unit comprising:
- a first introducing section into which the first liquid is introduced from the means for supplying the first liquid;
- a second introducing section into which the second liquid is introduced from the means for supplying the second liquid;
- a drain section for draining the first liquid;
- a liquid-transporting passage which is provided with a plurality of electrodes and which joins the first introducing section to the drain section and which is filled with a gas;
- a measurement section provided in at least a part of the liquid-transporting passage; and
- a voltage application means for applying a voltage to at least a part of the plurality of electrodes;

a third unit comprising a detection system arranged adjacent to the measurement section; and
a fourth unit for draining liquid from the drain section, and
wherein the second liquid is immiscible with the first liquid;
wherein the means for supplying the first liquid discharges the first liquid as to fractionate of the same;
wherein the means for supplying the second liquid discharges the second liquid as to fractionate of the same;
wherein the first liquid being fractured by the means for supplying the first liquid and the first liquid being contained by at least a part of the second liquid;
wherein the first liquid being contained by at least a part of the second liquid is fractured by gas of a periphery in the liquid-transporting passage of the second unit, and
wherein the voltage application means applies a voltage to at least a part of the plurality of electrodes so as to move the first liquid from the first introducing section to the second introducing section along the liquid-transporting passage, and also as to move the first liquid along the liquid-transporting passage.

10. The system for analyzing according to claim 9, wherein the first liquid comprises a sample and a reagent, and the first introducing section has a plurality of entry ports for separately introducing the sample and the reagent.

11. The system for analyzing according to claim 9, wherein the voltage application means applies a voltage as to transport a first liquid which is contained by at least a part of a second liquid, the second liquid being introduced into a plurality of the second introducing sections, and as for the first liquid which is contained by at least a part of a second liquid, the second liquid being introduced into a plurality of the second introducing sections, the periphery of the second liquid which contains the first liquid is filled with the gas.

12. The system for analyzing according to claim 9, wherein the means for supplying the first liquid has a first probe which sucks and discharges the first liquid, and the means for supplying the second liquid has a second probe which sucks and discharges the second liquid.

13. The system for analyzing according to claim 12, wherein the first probe discharges the first liquid to the first introducing section, and the second probe discharges the second liquid to the second introducing section.

* * * * *